(12) United States Patent
Jamieson et al.

(10) Patent No.: US 7,632,519 B2
(45) Date of Patent: Dec. 15, 2009

(54) TRPV1 AGONIST COMPOUNDS, FORMULATIONS, PRODRUGS, METHODS FOR USING THE SAME

(75) Inventors: Gene Curtis Jamieson, Boulder Creek, CA (US); Naweed Muhammad, Fremont, CA (US); Keith R. Bley, Mountain View, CA (US)

(73) Assignee: NeurogesX, Inc., San Mateo, CA (US)

( * ) Notice: Subject to any disclaimer, the term of this patent is extended or adjusted under 35 U.S.C. 154(b) by 200 days.

(21) Appl. No.: 11/411,328

(22) Filed: Apr. 25, 2006

(65) Prior Publication Data

US 2006/0240097 A1    Oct. 26, 2006

Related U.S. Application Data

(60) Provisional application No. 60/675,027, filed on Apr. 25, 2005.

(51) Int. Cl.
*A61K 9/48* (2006.01)
(52) U.S. Cl. .......................... 424/451; 514/534; 554/63
(58) Field of Classification Search ................. 424/451; 514/534; 554/63
See application file for complete search history.

(56) References Cited

U.S. PATENT DOCUMENTS

| 4,493,848 | A | * | 1/1985 | LaHann et al. | ............... 514/627 |
|---|---|---|---|---|---|
| 4,544,669 | A | * | 10/1985 | LaHann et al. | ............... 514/563 |
| 5,094,782 | A | | 3/1992 | Chen et al. | |
| 2003/0064122 | A1 | | 4/2003 | Goldberg et al. | |
| 2004/0122089 | A1 | | 6/2004 | Martin et al. | |
| 2006/0034872 | A1 | | 2/2006 | Woolf | |

FOREIGN PATENT DOCUMENTS

| EP | 0 132 115 A1 | 1/1985 |
|---|---|---|
| EP | 0 132 115 B1 | 1/1985 |
| EP | 0 132 346 A1 | 1/1985 |
| EP | 0 132 346 B1 | 1/1985 |
| EP | 0 149 544 A2 | 7/1985 |
| EP | 0 149 544 A3 | 7/1985 |
| EP | 0 149 544 B1 | 7/1985 |
| EP | 1 437 344 A1 | 7/2004 |
| EP | 1437344 * | 7/2004 |
| GB | 2 168 976 A | 7/1986 |
| GB | 2168976 * | 7/1986 |
| JP | 10-114649 A | 5/1998 |

(Continued)

OTHER PUBLICATIONS

Hammell, D.C. et al. (Jun. 18, 2004). "A Duplex "Gemini" Prodrug of Naltrexone for Transdermal Delivery," J. Control Release 97(2):283-290.*

(Continued)

*Primary Examiner*—Deborah D Carr
(74) *Attorney, Agent, or Firm*—Morrison & Forester LLP

(57) ABSTRACT

Described here are TRPV1 agonist compounds and their methods of synthesis and use. In addition to specifically identified compounds, capsaicin prodrugs, gemini dimers, and mutual prodrugs are also described. Formulations of the TRPV1 agonist compounds may be in the form of a liquid, tablets, capsules, gel, cream, emulsion, a patch, or the like. Methods for treating medical conditions using the compounds, compositions, or prodrugs described, are also provided.

46 Claims, 37 Drawing Sheets

FOREIGN PATENT DOCUMENTS

| | | | |
|---|---|---|---|
| JP | 10114649 | * | 5/1998 |
| JP | 10120558 | * | 5/1998 |
| JP | 2003-055314 A | | 2/2003 |
| WO | WO-03/102156 A2 | | 12/2003 |
| WO | WO-03/102156 A3 | | 12/2003 |
| WO | WO-03/102156 B1 | | 12/2003 |
| WO | WO03102156 | * | 12/2003 |

OTHER PUBLICATIONS

Otagiri, M. et al. (1999). "Improving the Pharmacokinetic and Pharmacodynamic Properties of a Drug by Chemical Conversion to a Chimera Drug," *J. Control Release* 62(1-2):223-229.*

Sloan, K.B. ed. (1992). Prodruqs: Topical and Ocular Druq Delivery, Marcel Dekker, Inc.:NY, NY, vol. 53, pp. vii-viii (Table of Contents Only.).*

Anand, P. (Sep. 2003). "Capsaicin and Menthol in the Treatment of Itch and Pain: Recently Cloned Receptors Provide the Key," *Gut* 52(9):1233-1235.

Bley, K.R. (2004). "Recent Developments in Transient Receptor Potential Vanilloid Receptor 1 Agonist-Based Therapies," *Expert Opin. Investig. Drugs* 13(11):1445-1456.

Carlton, S.M. et al. (May 1998). "Attenuation of Formalin-Induced Nociceptive Behaviors Following Local Peripheral Injection of Gabapentin," *Pain* 76(1-2):201-207.

Caterina, M.J. et al. (2001). "The Vanilloid Receptor: A Molecular Gateway to the Pain Pathway," *Annu. Rev. Neurosci.* 24:487-517.

Debreceni, A. et al. (1999). "Capsaicin Increases Gastric Emptying Rate in Healthy Human Subjects Measured by $^{13}$C-Labeled Octanoic Acid Breath Test," *J. Physiol.* (Paris) 93(5):455- 460.

Del Rosso, J.Q. (Mar. 2006). "Combination Topical Therapy for the Treatment of Psoriasis," *Journal of Drugs in Dermatology* 5(3):232-234.

Ellis, C.N. et al. (Sep. 1993). "A Double-Blind Evaluation of Topical Capsaicin in Pruritic Psoriasis," *J. Am. Acad. Dermatol.* 29(3):438-442.

Fukuhara, A. (1996). "Stereoselective Disposition of Flurbiprofen From a Mutual Prodrug with a Histamine $H_2$-Antagonist to Reduce Gastrointestinal Lesions in the Rat," *Chirality* 8(7):494-502.

Gonzalez, R. et al. (Jun. 1998). "Effect of Capsaicin-Containing Red Pepper Sauce Suspension on Upper Gastrointestinal Motility in Healthy Volunteers," *Dig. Dis. Sci.* 43(6):1165-1171.

Hammell, D.C. et al. (Jun. 18, 2004). "A Duplex "Gemini" Prodrug of Naltrexone for Transdermal Delivery," *J. Control Release* 97(2):283-290.

Hughes, S.R. et al. (Sep. 4, 1992). "Olvanil: More Potent than Capsaicin at Stimulating the Efferent Function of Sensory Nerves," *Eur. J. Pharmacol.* 219(3):481-484.

Jordt, S-E. et al. (Aug. 2003). "Lessons from Peppers and Peppermint: The Molecular Logic of Thermosensation," *Curr. Opin. Neurobiol.* 13(4):487-492.

Nelson, A.G. et al. (2000). "The Effect of Capsaicin on the Thermal and Metabolic Responses of Men Exposed to 38°C. for 120 Minutes," *Wilderness Environ. Med.* 11(3):152-156.

Otagiri, M. et al. (1999). "Improving the Pharmacokinetic and Pharmacodynamic Properties of a Drug by Chemical Conversion to a Chimera Drug," *J. Control Release* 62(1-2):223-229.

Sathyanarayana, M.N. (2006). "Capsaicin and Gastric Ulcers," *Crit. Rev. Food Sci. Nutr.* 46(4):275-328.

Sloan, K.B. ed. (1992). *Prodrugs: Topical and Ocular Drug Delivery*, Marcel Dekker, Inc.:NY, NY, vol. 53, pp. vii-viii (Table of Contents Only.).

Walpole, C.S.J. et al. (Jul. 19, 1996). "Similarities and Differences in the Structure-Activity Relationships of Capsaicin and Resiniferatoxin Analogues," *J. Med. Chem.* 39(15):2939-2952.

Baldessari A. et al. (1987). "C NMR Spectral Data of Some N-Vanillyl-, N-Piperonyl- and N-Veratryl-Alkylaminoalkylamides," *Magn. Res. Chem.* 25:1012-1018.

Bennett, D.J. et al. (1968). "Constitution and Biosynthesis of Capsaicin," *J. Chem. Soc. C.* 1:442-446.

Brand, L. et al. (1987). "NE-19550: A Novel, Orally Active Anti-Inflammatory Analgesic," *Drugs Under Experimental and Clinical Research* 13(5):259-265.

Carr, J.L. et al. (Jan. 1, 2006). "In vitro Photo-Release of a TRPV1 Agonist," *Bioorganic & Medicinal Chemistry Letters* 16(1):208-212.

Chen, I.J. et al. (Apr.-May 1992). "Hypotensive and Antinociceptive Effects of Ether-Linked and Relatively Non-Pungent Analogues of N-nonanoyl Vanillylamide," *European Journal of Medicinal Chemistry* 27(3):187-192.

Couch, M.W. et al. (1972). "Mass Spectrometry of Benzylamines and Benzylamine Derivatives," *Org. Mass. Spectrometry* 6:21-32.

Couch, M.W. et al. (Jan.-Mar. 1972). "N-Ethyl-N-(Trimethylsilyl)Benzylamine," *Arch. Mass. Spectral Data* 3(1):32-33.

Furuya, I. et al. (2003)."Preparation of Nonvolatile Stable Odorless Nonirritating Esters of Hydroxycinnamic Acid Derivatives and Their Use as Antioxidants," *CAPLUS* 2003:143380, two pages.

International Search Report mailed Oct. 26, 2006, for PCT Application No. PCT/US2006/015785, filed Apr. 25, 2006, nine pages.

Jones, E.C.S. et al. (1925). "The Relation Between Chemical Constitution and Pungency in Acid Amides," *J. Chem. Soc.* 127(II):2588-2598.

Kosuga, M. et al. (1998). "Agents Enhancing Bioactivity of Shineki (Meaning Water in Chinese Medicine) Containing Benzene Derivatives and Their Compositions," *CAPLUS* 1998:274844, two pages.

Micko (1899). *Chem Zentralbl.* 70(I):293-294.

Substance Identification: Beilstein Registry No. 2943902, *Beilstein Institut zur Foerderung der Chemischen Wissenschaften*, two pages, 1987.

Substance Identification: Beilstein Registry No. 3111367, *Beilstein Institut zur Foerderung der Chemischen Wissenschaften*, one page, 1968.

Substance Identification: Beilstein Registry No. 3112056, *Beilstein Institut zur Foerderung der Chemischen Wissenschaften*, two pages, 1968.

Substance Identification: Beilstein Registry No. 3455977, *Beilstein Institut zur Foerderung der Chemischen Wissenschaften*, two pages, 1925.

Substance Identification: Beilstein Registry No. 3491177, *Beilstein Institut zur Foerderung der Chemischen Wissenschaften*, two pages, 1899.

Wu, P.C. et al. (Feb. 1997). "Development and Evaluation of Transdermal Patches of Nonivamide and Sodium Nonivamide Acetate," *Die Pharmazie* 52(2):135-138.

Zhao, J. et al. (Apr. 18, 2006). "Caged Vanilloid Ligands for Activation of TRPV1 Receptors by 1- and 2-Photon Excitation," *Biochemistry* 45(15):4915-4926.

* cited by examiner

ATLANTIC MICROLAB, INC.

Sample No. MTE-Mor2t 5 t-11-18  
SUBMITTER  
Company/School: Cardarelli Health  
Address: 1401 Magellan Lab Dr  
NC 27260

P.O. Box 2218  
Norcross, Georgia 30091  NO CHARGE FOR DUPLICATES  
(770) 242-0082  
www.atlanticmicrolab.com  
PROFESSOR/SUPERVISOR:  
P.O. #:

NAME: Itzli    DATE 7/22/04

| Element | Theory | Found | |
|---|---|---|---|
| C | 68.44 | 67.98 | 67.87 |
| H | 8.16 | 8.22 | 8.19 |
| N | 4.20 | 4.21 | 4.18 |
|   | — |   |   |

Single ☒  Duplicate ☐  
Elements Present: C H N O  
Analyze for: C H N  
Hygroscopic ☒  Explosive ☐  
M.P.    B.P.  
To be dried: Yes ☐  No ☒  
Temp.    Time  
FAX Service ☒  919-481-9708  
FAX Phone #:  
Rush Service ☒  (SEE CURRENT PRICE LIST)  
Phone Service ☐  
Phone No.

Date Completed: JUL 23 2004  
Date Received: JUL 23 2004  
Remarks:

$C_9H_{17}NO_4 \cdot 0.1\, H_2O$ : Calculated for

```
Data File D:\HPCHEM\1\DATA\MRD\07090004.D                      Sample Name: NTF-M21-1-4-8
========================================================================================
Injection Date   : 7/9/2004 2:23:05 PM             Seq. Line  :  4
Sample Name      : NTF-M21-1-4-8                   Location   : Vial 3
Acq. Operator    : JLI                                   Inj  :  1
                                                 Inj Volume  : 20 µl
Sequence File    : C:\HPCHEM\1\SEQUENCE\MRD37JIE.S
Method           : C:\HPCHEM\2\METHODS\NTFM0021.M
Last changed     : 7/9/2004 11:53:23 AM by JLI
Alltima C18 5 micron, 250x4.60 mm, A1: water, 0.1% TFA, B2: 0.1% TFA in ACN, 1.0 ml/min
flow rate, 20 microliter injection volume.
Time     %B       Flow
0        0.00     1.000
5.00     100.0    1.000
10.00    100.0    1.000
12.00    100.0    1.000
14.00    0.0      1.000
16.00    0.0      1.000
```

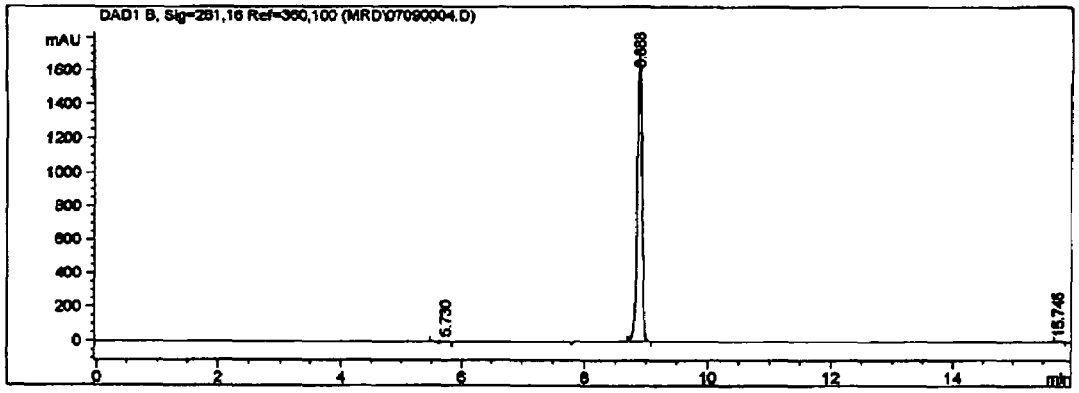

```
                           Area Percent Report

Sorted By              :    Retention Time
Multiplier             :    1.0000
Dilution               :    1.0000

Signal 1: DAD1 B, Sig=281,16 Ref=360,100

Peak  RetTime  Sig  Type     Area        Height       Area
 #    [min]              [mAU*s]       [mAU]         %
----|--------|---|----|-----------|-----------|--------|
  1   5.730   1   BP       26.90792     5.16442    0.2902
  2   8.868   1   BB     9237.93262  1741.60510   99.6338
  3  15.745   1   PB        7.04313     3.96436    0.0760

Totals :                9271.88366  1750.73389

Results obtained with enhanced integrator!
===========================================================================
                           Summed Peaks Report
===========================================================================
```

ATLANTIC MICROLAB, INC.

Sample No. NTF-ncol-SD-14-8

P.O. Box 2288
Norcross, Georgia 30091
(770) 242-0082
www.atlanticmicrolab.com

PROFESSOR/SUPERVISOR:
P.O. #:

SUBMITTER
Company / School: Central Health
Address: 160 N Mepellen Lab Ct.
Morrisville
NC 27560

NAME: Teli   DATE: 7/22/04

Single ☒  Duplicate ☐
Elements Present: CHNO
Analyze for: CHN
Hygroscopic ☒  Explosive ☐
M.P.    B.P.
To be dried: Yes ☐  No ☒
Temp._____  Time_____
FAX Service ☒  912-491-4308
FAX Phone #
Rush Service ☒  (SEE CURRENT PRICE LIST)
Phone Service ☐
Phone No.

Date Completed: JUL 23 2004

| Element | Theory | Found |
|---|---|---|
| C | 69.78 | 69.56 |
| H | 8.64 | 8.74 |
| N | 3.87 | 3.92 |
|  |  |  |
|  |  |  |
|  |  |  |

Date Received: JUL 23 2004
Remarks:

```
Data File D:\HPCHEM\1\DATA\MRD\07120002.D          Sample Name: NTF-M21-1-5-21

Injection Date  : 7/12/2004 12:46:50 PM      Seq. Line  :   2
Sample Name     : NTF-M21-1-5-21             Location   : Vial 1
Acq. Operator   : JLI                        Inj        :   1
                                             Inj Volume :  20 µl
Sequence File   : C:\HPCHEM\1\SEQUENCE\MRD37JIE.S
Method          : C:\HPCHEM\2\METHODS\NTFM0021.M
Last changed    : 7/9/2004 11:53:23 AM by JLI
Alltima C18 5 micron, 250x4.60 mm, A1: water, 0.1% TFA, B2: 0.1% TFA in ACN, 1.0 ml/min
flow rate, 20 microliter injection volume.
Time    %B     Flow
0       0.00   1.000
5.00    100.0  1.000
10.00   100.0  1.000
12.00   100.0  1.000
14.00   0.0    1.000
16.00   0.0    1.000
```

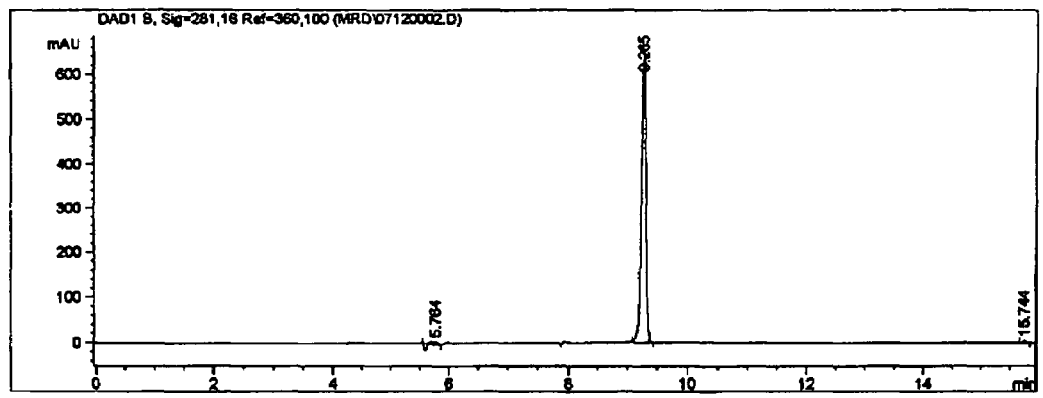

```
                          Area Percent Report

Sorted By           :      Retention Time
Multiplier          :      1.0000
Dilution            :      1.0000

Signal 1: DAD1 B, Sig=281,16 Ref=360,100

Peak RetTime Sig Type    Area      Height     Area
 #   [min]            [mAU*s]     [mAU]       %
----|-------|---|----|----------|----------|--------|
 1   5.764   1  BP      25.64572    5.82803  0.7684
 2   9.265   1  BB    3301.39355  652.48108 98.9154
 3  15.744   1  BB      10.55314    4.40007  0.3162

Totals :              3337.59242  662.70917

Results obtained with enhanced integrator!
                          Summed Peaks Report
```

FIG. 21

ATLANTIC MICROLAB, INC.

Sample No. NIF-mod1-SD-1-S-2

SUBMITTER
Company/School: Gaolord Hurles
Address: 1601 Mayflower Lab Ct.
Martinsville
NC 27050

NAME: Jie Li          DATE: 7/21/04

P.O. Box 2288
Norcross, Georgia 30091
(770) 242-0162
www.atlanticmicrolab.com

PROFESSOR/SUPERVISOR:
P.O. #:

Single ☒  Duplicate ☐
Elements Present: CHNO
Analyze for: CHN
Hygroscopic ☒  Explosive ☐
M.P.           B.P.
To be dried: Yes ☐  No ☒
Temp.         Yes     No ☒   Time
FAX Service ☒
FAX Phone #: 10-481-4908
Rush Service ☒  (SEE CURRENT PRICE LIST)
Phone Service ☐
Phone No.

| Element | Theory | Found |
|---------|--------|-------|
| C | 70.37 | 70.29 |
| H | 8.86 | 8.90 |
| N | 3.75 | 3.75 |
| | | |
| | | |
| | | |

Date Received: JUL 22 2004         Date Completed: JUL 22 2004
Remarks:

FIG. 25

```
Data File D:\HPCHEM\1\DATA\MRD\07140002.D              Sample Name: NTF-M21-1-6-34
================================================================================
Injection Date  : 7/14/2004 4:35:53 PM         Seq. Line :   2
Sample Name     : NTF-M21-1-6-34               Location  : Vial 2
Acq. Operator   : JLI                              Inj  :   1
                                              Inj Volume :  20 µl
Sequence File   : C:\HPCHEM\1\SEQUENCE\MRD37JIE.S
Method          : C:\HPCHEM\2\METHODS\NTFM0021.M
Last changed    : 7/9/2004 11:53:23 AM by JLI
Alltima C18 5 micron, 250x4.60 mm, A1: water, 0.1% TFA, B2: 0.1% TFA in ACN, 1.0 ml/min
flow rate, 20 microliter injection volume.
Time    %B      Flow
0       0.00    1.000
5.00    100.0   1.000
10.00   100.0   1.000
12.00   100.0   1.000
14.00   0.0     1.000
16.00   0.0     1.000
```

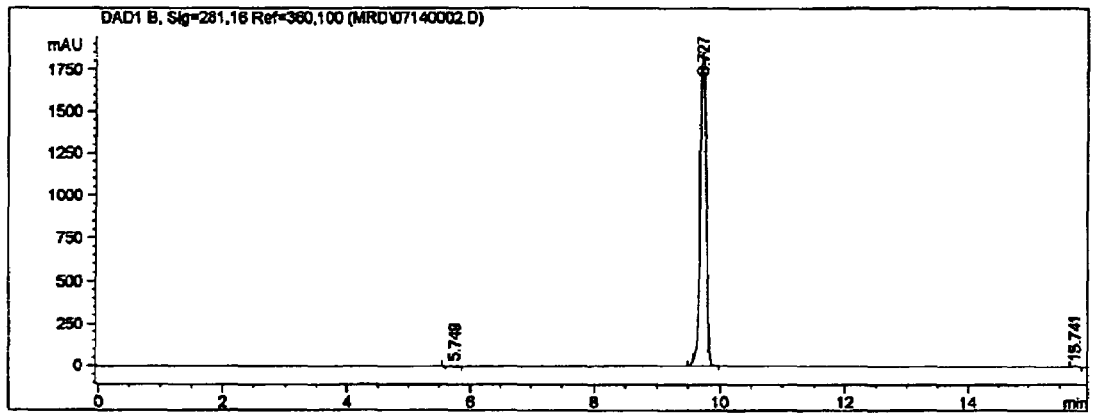

```
                           Area Percent Report

Sorted By          :     Retention Time
Multiplier         :     1.0000
Dilution           :     1.0000

Signal 1: DAD1 B, Sig=281,16 Ref=360,100

Peak RetTime Sig Type   Area        Height      Area
 #   [min]            [mAU*s]      [mAU]         %
----|-------|---|----|----------|----------|--------|
  1   5.749  1  BP     32.35292    6.21842    0.2712
  2   9.727  1  BB   1.18864e4  1851.36890   99.6297
  3  15.741  1  PB     11.82797    4.40469    0.0991

Totals :                1.19306e4  1861.99201

Results obtained with enhanced integrator!
                          Summed Peaks Report
```

ATLANTIC MICROLAB, INC.

Sample No. NTF-M021-SD-1-6-34

P.O. Box 2288
Norcross, Georgia 30091
(770) 242-0082
www.atlanticmicrolab.com

PROFESSOR/SUPERVISOR:
P.O. #:

SUBMITTER
Company/School: Cockrell Health
Address: 160 N Magellan Lab Ct
Montisville
NC 27106

NAME: Tisli          DATE: 2/24/04

| Element | Theory | Found | | | |
|---|---|---|---|---|---|
| C | 70.92 | 7063 | | | |
| H | 9.06 | 922 | | | |
| N | 3.60 | 365 | | | |
| | | | | | |
| | | | | | |
| | | | | | |

Single ☒   Duplicate ☐
Elements
Present: C H N O
Analyze for: C H N
Hygroscopic ☒   Explosive ☐
M.P. ___   B.P. ___
To be dried: Yes ☐  No ☒
Temp. ___ Vac. ___ Time ___
FAX Service ☒   FAX Phone #: 917-441-4708
Rush Service ☒   (SEE CURRENT PRICE LIST)
Phone Service ☐
Phone No.

JUL 23 2004

Date Received: JUL 2 3 2004
Remarks:

Date Completed: JUL 23 2004

FIG. 26

ATLANTIC MICROLAB, INC.

Sample No. NTF-Mnpl-sp+8-32

SUBMITTER
Company/School: Carolinas Health
Address: 16oN Medallion Lab Ct.
Montsville
NC 27606
NAME: Tieli  DATE 7/21/04

P.O. Box 2288
Norcross, Georgia 30091
(770) 242-0082
www.atlanticmicrolab.com
PROFESSOR/SUPERVISOR:
P.O. #:

Single ☒  Duplicate ☐

Elements Present: C, H, N, O
Analyze for: C H N
Hygroscopic ☒  Explosive ☐
M.P.  B.P.
To be dried: Yes ☐  No ☒
Temp.  Vac.  Time
FAX Service ☒  FAX Phone # 91 - 91 - 4208
Rush Service ☒ (SEE CURRENT
Phone Service ☐  PRICE LIST)
Phone No.

| Element | Theory | Found | |
|---------|--------|-------|---|
| C | 75.61 | 75.50 | |
| H | 10.15 | 10.79 | |
| N | 2.45 | 2.44 | |
| | | | |
| | | | |
| | | | |
| | | | |

Date Received: JUL 22 2004    Date Completed: JUL 2 2 2004
Remarks:

FIG. 31

TRPV1 AGONIST COMPOUNDS, FORMULATIONS, PRODRUGS, METHODS FOR USING THE SAME

CROSS REFERENCE TO RELATED APPLICATION

This application claims priority to U.S. Provisional Application No. 60/675,027 filed on Apr. 25, 2005, which is incorporated herein by reference in its entirety.

FIELD

The compounds and methods described here relate to capsaicinoids and their related esters (e.g., aliphatic esters, hydrophilic esters, and the like), gemini dimers, and prodrugs (e.g., PEGylated prodrugs, mutual prodrugs with or without a linker moiety, and the like) and to methods for their synthesis and use.

BACKGROUND

Capsaicin is the pungent ingredient in chili peppers. It is a highly selective agonist for transient receptor potential vanilloid 1 receptor (TRPV1; formerly known as vanilloid receptor 1 (VR1)), a ligand-gated, non-selective cation channel preferentially expressed on small-diameter sensory neurons, especially those C-fibers which specialize in the detection of painful or noxious sensations. TRPV1 responds to noxious stimuli including capsaicin, heat, and extracellular acidification, and will integrate simultaneous exposures to these stimuli. (See: Caterina M J, Julius D. The vanilloid receptor: a molecular gateway to the pain pathway. *Annu Rev Neurosci.* 2001. 24:487-517). The initial effect of the activation of TRPV1-expressing (capsaicin-sensitive) nociceptors are burning sensations, hyperalgesia, allodynia, and erythema. However, after prolonged exposure to low-concentration capsaicin or single exposures to high-concentration capsaicin or other TRPV1 agonist, the small-diameter sensory axons become less sensitive to a variety of stimuli, including capsaicin or thermal stimuli. This prolonged exposure is also characterized by reduced pain responses. These later-stage effects of capsaicin are frequently referred to as "desensitization" and are the rationale for the development of capsaicin formulations for the treatment of various pain syndromes and other conditions. (See: Bley K R. Recent developments in transient receptor potential vanilloid receptor 1 agonist-based therapies. *Expert Opin Investig Drugs.* 2004. 13(11):1445-1456).

Capsaicin, capsaicinoids and TRPV1 agonists may be useful for amelioration of a plurality of diseases. For example, they may be used to treat neuropathic pain (including pain associated with diabetic neuropathy, postherpetic neuralgia, HIV/AIDS, traumatic injury, complex regional pain syndrome, trigeminal neuralgia, erythromelalgia and phantom pain), pain produced by mixed nociceptive and/or neuropathic mixed etiologies (e.g., cancer), osteoarthritis, fibromyalgia, lower back pain, inflammatory hyperalgesia, vulvar vestibulitis or vulvodynia, sinus polyps interstitial cystitis, neurogenic or overactive bladder, prostatic hyperplasia, rhinitis, surgery, trauma, rectal hypersensitivity, burning mouth syndrome, oral mucositis, herpes (or other viral infections), prostatic hypertrophy, dermatitis, pruritus, itch, tinnitus, psoriasis, warts, cancers (especially skin cancers), headaches, and wrinkles.

Numerous delivery devices and formulations are available or are being developed to deliver capsaicin. However, one of the problems with many of these devices and formulations is the concomitant pain (a burning sensation due to the pungency of the drug) associated with the administration of the capsaicin or other TRPV1 agonist. In addition, many of these formulations and devices are not suitable for prolonged or sustained delivery.

Accordingly, it would be desirable to provide improved delivery devices and formulations, which have the potential for reduced pungency associated with the administration of a TRPV1 agonist. In addition, it would be desirable to provide improved delivery devices and formulations that have improved dermal pharmacokinetics and prolonged or sustained delivery capability to the intended site of action. Finally, in some cases it would be desirable to deliver another pharmacologically active compound along with capsaicin, a capsaicinoid, or other TRPV1 agonist.

SUMMARY

One way of minimizing or eliminating the inherent pungency of capsaicin, its analogs and other TRPV1 agonists, is to modify the chemical structure of the parent molecule such that the parent drug is released after its structural derivative has been delivered to the body and/or after it has reached its site of action. The chemical-release kinetics of a parent drug may impart two important properties: (a) reduced and/or delayed pungency and (b) prolonged and slow release for extended duration of pharmacological activity. Such structural modifications eliminate the reliance on special requirements for formulations or delivery devices in order to reduce the acute pungency associated with the administration of TRPV1 agonists. However, such formulations and delivery device techniques can be used to further improve the characteristics of drug delivery and/or patient comfort as well.

Thus the capsaicin, capsaicinoids or other TRPV1 agonist compounds described herein are chemically modified to control the rate at which the capsaicin, capsaicinoid, or other TRPV1 agonist is bioavailable through enzymatic and/or hydrolytic conversions. In addition, the pungency and/or efficacy of the capsaicin, capsicinoid, or other TRPV1 agonist may be controlled by selection of a derivative that could display either a particular rate of hydrolysis and/or restricted access to the agonist binding site on TRPV1 and/or the ability to activate TRPV1 if the compound were to bind to the receptor. For example, an ester or other hydrolyzable linker group may be covalently bonded to the phenol position of capsaicin, a capsaicinoid, or structurally similar TRPV1 agonists such that upon administration, enzymes and/or water may induce hydrolysis of the linkage to liberate the parent drug (capsaicin, a capsaicinoid, or other TRPV1 agonist, as the case may be). Linker groups may be constituted by simple esters or more complex functional groups that are sensitive to enzymatic systems and/or simple aqueous hydrolysis. With ester prodrugs, the pungency could be delayed substantially beyond the treatment phase or could be reduced to levels that might not require rescue medications or pre-treatment topical anesthetic.

Formulations containing prodrugs of capsaicin or other vanilloids should be well tolerated while producing the necessary beneficial therapeutic effect(s) similar to the parent drug. In addition, the physicochemical properties of the modified capsaicinoid may improve dermal uptake by decreased hydrogen bonding and increased partition into lipids relative to water. Similar improvements have been noted for dermal applications of other prodrugs. See Sloan, K. B. 1992. *Topical and Ocular Drug Delivery*, Marcel Dekker, New York.

Prodrugs of several drugs and health products have been marketed or are subject to clinical investigation. Examples include naltrexone, ketoprofen, ester C, ester E and propranolol. The advantages cited for these products include improved tolerability, increased bioavailability, and efficacy. Prodrugs of capsaicin may exhibit many of the same improved characteristics. The phenolic hydroxyl group at position 4 on the aromatic ring of the capsaicin molecule is a highly accessible target for chemical modifications, leading to physicochemical and pharmacological enhancements. For example, some attributes governing targeted drug delivery and pharmacological response are: (1) receptor site binding, (2) micropharmacokinetics (localization within a cell or tissue compartment), (3) residence time at site of action or other tissues, (4) metabolic and renal clearance rates, and (5) dose response.

With the capsaicin, capsaicinoid or other TRPV1 agonist described here, the active agent is either delivered to the site of action following bioconversion of the prodrug, or bioconversion takes place after it has reached the site of action, or it is combination of these two bioconversion patterns. Thus the capsaicin, capsaicinoids, or other TRPV1 agonists described here may be delivered slowly over time to mitigate the burst of pungency associated with a rapid exposure to capsaicin or other capsaicinoids and TRPV1 agonists. The prodrug derivative may be synthesized so that it does not bind with the TRPV1 receptor (e.g., due to limited accessibility to the binding site) and/or so that binding does not elicit significant TRPV1 activation. Structural requirements for binding to TRPV1 have been evaluated (See: Walpole C S, Bevan S, Bloomfield G, Breckenridge R, James I F, Ritchie T, Szallasi A, Winter J, Wrigglesworth R. Similarities and differences in the structure-activity relationships of capsaicin and resiniferatoxin analogues. *J Med Chem.* 1996. 39(15):2939-2952). In the aromatic portion of TRPV1 ligands, deliberate structural variations have demonstrated the necessity of the juxtaposition of 4-hydroxy and 3-methoxy groups to maintain TRPV1 binding and resulting receptor agonism. Substitution of the free hydroxyl (including simple alkylation) resulted in diminished binding. In some of the variations we describe herein, we intentionally derivatize the 4-hydroxy position with a labile ester or other hydrolyzable group to block the TRPV1 binding, thereby mitigating the immediate pungent response. In these variations, the derivative linker group is hydrolyzed to release free capsaicin in a controlled manner governed by the inherent and specific nature of that linker. In addition to modifying time of onset of receptor site binding of capsaicin or capsaicinoids, substantially more drug may be administered for slow and sustained release over a longer duration. Such a release profile would be difficult to tailor without altering the physicochemical properties of the parent drug through chemical modification(s).

With this approach, pungency and concomitant neurogenic inflammation should be manageable. That is, the compounds described herein may result in there being no substantial treatment-related pain. Similarly, the pungency could be delayed or reduced, or even span over a long duration with low or negligible intensity. In addition, the use of the compounds and formulations described herein may obviate the need for local anesthetic pretreatment when TRPV1 agonists are being administered. Similarly, the use of the described compounds and formulations may obviate or reduce the need for strong rescue medication to control treatment-related pain.

Accordingly, described here are capsaicinoid compounds and their methods of synthesis and use. In some variations, the compound has the following formula:

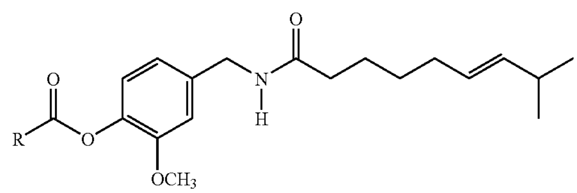

where R is selected from the group consisting of hydrogen and a substituted or unsubstituted, saturated or unsaturated, linear or branched, $C_2$-$C_{20}$ alkyl. In some variations, R is selected specifically from the group consisting of hydrogen, ethyl, propyl, isopropyl, butyl, t-butyl, and isobutyl. In yet other variations, R is $—(CH_2)_nCH_3$ and n is an integer from 1-19, an integer from 2-5, an integer from 6-10, or an integer from 11-19. Formulations of these compounds are also described, where the formulation is a liquid, tablet, capsule, gel, cream, emulsion, patch or the like.

Other compounds are described having the formula:

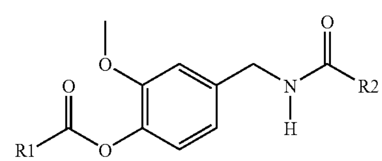

where R1 is selected from the group consisting of hydrogen and a substituted or unsubstituted, saturated or unsaturated, linear or branched $C_1$-$C_{20}$ alkyl and R2 is selected from the group consisting of a substituted or unsubstituted, saturated or unsaturated, linear or branched, $C_1$-$C_{20}$ alkyl. In both R1 and R2, when the alkyl group is unsaturated, each unsaturated bond may have either the cis or trans configuration, independent of the configuration of other unsaturated bonds.

Similarly, other compounds are described having the formula:

where R1 is itself an active agent. In some variations, R1 is a calcium channel modulator/anticonvulsant such as gabapentin or pregabalin and the like. In some other variations, the prodrug moiety R1 is an analgesic/anti-inflammatory such as ibuprofen, ketoprofen, flurbiprofen, salicylic acid, acetylsalicylic acid, diflunisal, fenoprofen, etodolac, indomethacin, mefenamic acid, naproxen, sulindac or the like. R2 is selected from the group consisting of a substituted or unsubstituted, linear or branched, $C_1$-$C_{20}$ alkyl. When R2 is an unsaturated alkyl group, each unsaturated bond may be either in the cis or trans configuration, independent of other unsaturated bonds. In some variations, R2 is (3E)-2-methyloct-3-ene or (3Z)-2-methyloct-3-ene or n-octane.

Similarly, the compounds may have the following formula:

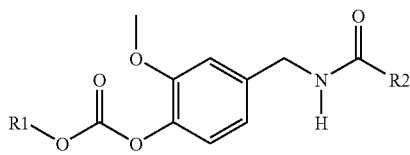

where R1 is a prodrug moiety and is an active agent linked to capsaicin through a linker such a hydroxyformic acid. In one variation, R1 is an opioid receptor agonist or antagonist such as nalbuphine, pentazocine, butorphanol, dezocine, bupernorphine, naltrexone, levorphanol, morphine, cyclorphan, levallorphan, cylazocine, naloxone, nalmephene, nalorphine, oxilorphan, phenazocine, loperamide, codeine, hydromorphone, epomorphine, normorphine, etorphine and tramadol. R2 is selected from the group consisting of a substituted or unsubstituted, saturated or unsaturated, linear or branched, $C_1$-$C_{20}$ alkyl. When R2 is an unsaturated alkyl group, each unsaturated bond may be either in the cis or trans configuration, independent of other unsaturated bonds.

In some variations, R2 is (3E)-2-methyloct-3-ene or (3Z)-2-methyloct-3-ene or n-octane.

In some variations, the prodrug moiety is an opioid. This can be prepared by reacting equimolar amount mounts of a TRPV1 agonist and an opioid with trichloromethyl chloroformate in anhydrous dichloromethane at zero degrees centigrade while dropwise adding an excess of triethylamine at ambient temperature. The

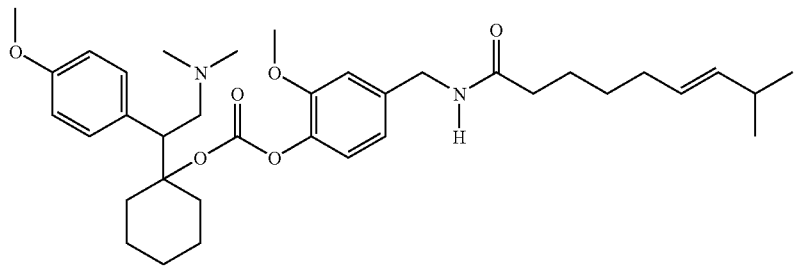

In another variation, R1 is a nonsteroidal anti-inflammatory agent such as acetaminophen, ethyl salicylate, methyl salicylate or piroxicam. In yet another variation, R1 is ketamine.

Gemini dimers and mutual prodrugs containing TRPV1 agonists may also be useful for the treatment of psoriasis. The efficacy of topical capsaicin for the treatment of psoriasis is well established (see, e.g., Ellis C N, Berberian B, Sulica V I, Dodd W A, Jarratt M T, Katz H I, Prawer S, Krueger G, Rex I H Jr, Wolf J E. A double-blind evaluation of topical capsaicin in pruritic psoriasis. *J Am Acad Dermatol*. 1993. 29(3):438-442). Other topical agents are also know and used to treat psoriasis (Del Rosso Do J Q. Combination topical therapy for the treatment of psoriasis. J Drugs Dermatol. 2006. 5(3):232-234). Accordingly, capsaicin, a capsaicinoid or a TRPV1 agonist in combination with other topical psoriasis therapies may display enhanced efficacy. By way of example, a mutual prodrug containing capsaicin and calcipotriene is shown here:

modified by covalent attachment of a prodrug moiety, wherein the prodrug moiety temporarily prohibits effective binding of capsaicin to the TRPV1 receptor. In other variations, the TRPV1 agonist prodrug comprises a TRPV1 agonist modified by covalent attachment of a prodrug moiety, wherein the prodrug moiety facilitates sustained release of the TRPV1 agonist.

In some variations, the prodrug moiety is attached to the TRPV1 agonist by substitution of the phenolic hydrogen of the TRPV1 agonist with the prodrug moiety. The prodrug moiety may be, for example, an acyl or an alkoxy. In some variations, it is an acyl. In yet other variations, the prodrug moiety is m-PEG. Formulations of these prodrugs are also described, and may be in the form of a liquid, tablet, capsule, gel, cream, emulsion, patch or the like. That is, the prodrugs may be formulated for topical, parenteral and oral use.

Similarly, gemini dimers of capsaicin are described herein. For background on gemini dimers, see: Hammell D C, Hamad M, Vaddi H K, Crooks P A, Stinchcomb A L. A duplex

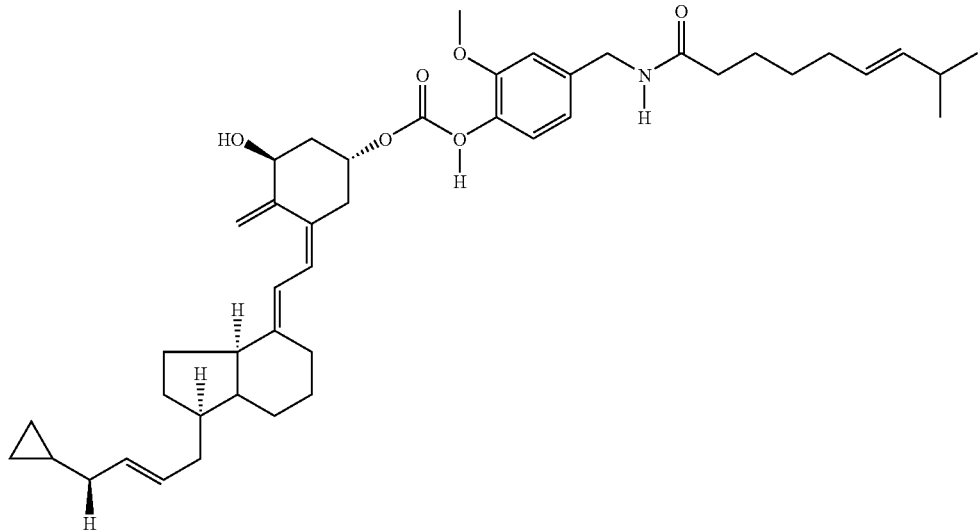

Mutual prodrugs of TRPV1 agonists and other antipsoriatic agents, such as other corticosteroids (effective in psoriasis) and anthralin are also described.

Formulations comprising these compounds are also described herein.

TRPV1 agonist prodrugs for use in the formulations and methods described herein are also provided. In one variation, the TRPV1 agonist prodrug comprises a TRPV1 agonist "Gemini" prodrug of naltrexone for transdermal delivery. J Control Release. 2004. 97(2):283-90. The formulations comprising the gemini dimer may be formulated as a liquid, tablets, capsules, gels, cream, emulsion, patches and the like.

Mutual prodrugs containing TRPV1 agonists are also described herein. (For a general description of mutual prodrugs, see: Otagiri M, Imai T, Fukuhara A. Improving the pharmacokinetic and pharmacodynamic properties of a drug by chemical conversion to a chimera drug. *J Control Release.* 1999. 62(1-2):223-229). For example, mutual prodrugs containing capsaicin and l-menthol are described herein. The formulations comprising the mutual prodrug may be formulated as liquids, tablets, capsules, gels, creams, emulsions, patches and the like.

Methods for treating various medical conditions or syndromes using the compounds, compositions, and formulations are also provided. In general, these methods comprise the step of delivering the compound or composition topically, parenterally, transmucosally, or orally. In some variations, the medical condition to be treated is pain, which includes but is not limited to pain associated with postherpetic neuralgia, diabetic neuropathy, HIV-associated neuropathy, complex regional pain syndrome, cancer, nerve injury, cancer chemotherapy, vulvodynia, trauma, surgery, chronic musculoskeletal pain, lower back pain, osteoarthritis or rheumatoid arthritis.

BRIEF DESCRIPTION OF THE DRAWINGS

FIG. 6 provides an elemental analysis of 4-[((6E)-8-methylnon-6-enoylamino)methyl]-2-methyoxyphenyl formate.

FIG. 11 provides an elemental analysis of 4-[((6E)-8-methylnon-6-enoylamino)methyl]-2-methyoxyphenyl acetate.

FIG. 15 is an HPLC analysis of 4-[((6E)-8-methylnon-6-enoylamino)methyl]-2-methyoxyphenyl propanoate.

FIG. 16 provides an elemental analysis of 4-[((6E)-8-methylnon-6-enoylamino)methyl]-2-methyoxyphenyl propanoate.

FIG. 20 is an HPLC analysis of 4-[((6E)-8-methylnon-6-enoylamino)methyl]-2-methyoxyphenyl butanoate.

FIG. 21 provides an elemental analysis of 4-[((6E)-8-methylnon-6-enoylamino)methyl]-2-methyoxyphenyl butanoate.

FIG. 25 is an HPLC analysis of 4-[((6E)-8-methylnon-6-enoylamino)methyl]-2-methyoxyphenyl 2,2-dimethylpropanoate.

FIG. 26 provides an elemental analysis of 4-[((6E)-8-methylnon-6-enoylamino)methyl]-2-methyoxyphenyl 2,2-dimethylpropanoate.

FIG. 31 is an elemental analysis of 4-[((6E)-8-methylnon-6-enoylamino)methyl]-2-methyoxyphenyl octadecanoate.

DETAILED DESCRIPTION

I. TRPV1 Compounds

Aliphatic Esters

Figure 1:
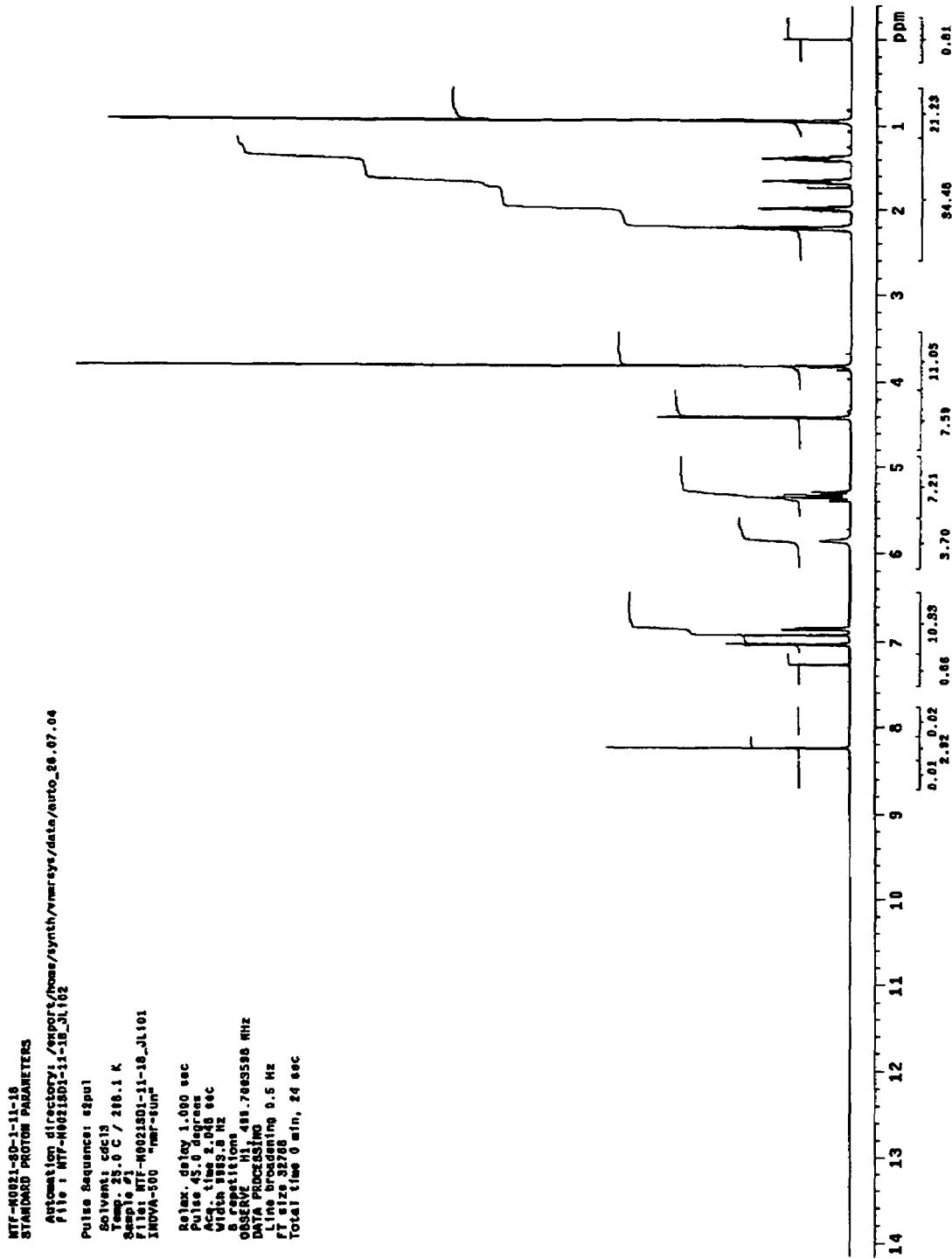
FIG. 1 provides a $^1$H-NMR of 4-[((6E)-8-methylnon-6-enoylamino)methyl]-2-methyoxyphenyl formate.

Described here are compounds, formulations and methods useful in treating pain and other medical conditions. Some compounds have the formula:

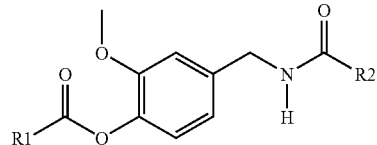

where R1 is selected from the group consisting of hydrogen and a substituted or unsubstituted, saturated or unsaturated, linear or branched $C_1$-$C_{20}$ alkyl and R2 is selected from the group consisting of a substituted or unsubstituted, saturated or unsaturated, linear or branched, $C_1$-$C_{20}$ alkyl. In both R1 and R2, when the alkyl group is unsaturated, each unsaturated bond may be in either the cis or trans configuration independent of other unsaturated bonds.

In some variations, R1 is selected specifically from the group consisting of hydrogen, ethyl, propyl, isopropyl, butyl, t-butyl, and isobutyl. In yet other variations, R1 is —$(CH_2)_n CH_3$ and n is an integer from 1-19, an integer from 2-5, an integer from 6-10, or an integer from 11-19. In some variations, R2 is (3E)-2-methyloct-3-ene or (3Z)-2-methyloct-3-ene -octane. Formulations of these compounds are also described, where the formulation is a liquid, tablet, capsule, gel, cream, emulsion, patch or the like.

Prodrugs of capsaicin, capsaicinoids and other TPRV1 agonist prodrugs are also described. In one variation, the prodrug comprises a TRPV1 agonist modified by covalent attachment of a prodrug moiety, wherein the prodrug moiety temporarily prohibits effective binding to or activation of TVRP1 by the agonist. In other variations, the prodrug comprises capsaicin, a capsaicinoid, or other TVRP1 agonist modified by covalent attachment of a prodrug moiety, wherein the prodrug moiety facilitates sustained release of capsaicin. In some variations, the prodrug comprises capsaicin or a capsaicinoid such as nonivamide, civamide, or olvanil (Hughes S R, Buckley T L, Brain S D. Olvanil: more potent than capsaicin at stimulating the efferent function of sensory nerves. *Eur J Pharmacol.* 1992. 219(3):481-484.) In other variations, the prodrug comprises a TRPV1 agonist, such as resiniferatoxin.

In some variations, the prodrug moiety is attached to the TRPV1 agonist by substitution of the phenolic hydrogen of the TRPV1 agonist with the prodrug moiety. The prodrug moiety may be, for example, an acyl or an alkoxy. In some variations, it is an acyl. Other prodrugs may be described by the following formula:

where R1 is selected from the group consisting of hydrogen and a substituted or unsubstituted, saturated or unsaturated, linear or branched $C_1$-$C_{20}$ alkyl and R2 is selected from the group consisting of a substituted or unsubstituted, saturated or unsaturated, linear or branched $C_1$-$C_{20}$ alkyl. In both R1 and R2, when alkyl group is unsaturated, each unsaturated bond may be either cis or trans configuration, independent of other unsaturated bonds.

Covalent linking of TRPV1 agonist with the prodrug moiety is in independent of the structure of R1 and R2.

In some variations, R1 is an acyl or an alkoxy. Formulations comprising these compounds are also described. In another variation, R1 is m-PEG. In yet another variation, R1 is capsaicin thus forming a "gemini" dimer of capsaicin. R2 is selected from the group consisting of a substituted or unsubstituted saturated or unsaturated, linear or branched, $C_1$-$C_{20}$ alkyl. In both R1 and R2, when the alkyl group is unsaturated, each unsaturated bond may either be in the cis or trans configuration, independent of other unsaturated bonds. In some variations, R2 is (3E)-2-methyloct-3-ene or (3Z)-2-methyloct-3-ene or n-octane. Any of these molecules may be included in a variety of pharmaceutically acceptable formulations, including liquids, tablets, capsules, gels, creams, emulsions, patches or the like.

In some variations, the phenolic hydrogen of resiniferatoxin is substituted by a prodrug moiety. The prodrug moiety may be, for example, an acyl or an alkoxy. In some variations, it is an acyl. Other prodrugs may be described by the following formula:

where R1 is selected from the group consisting of a substituted or unsubstituted, saturated or unsaturated, linear or branched $C_1$-$C_{20}$ alkyl. In some variations, R1 is an acyl or an alkoxy. In another variation, R1 is m-PEG. In yet another variation, R1 is capsaicin. Formulations comprising these compounds are also described. Any of these molecules may be included in a variety of pharmaceutically acceptable formulations, including liquids, tablets, capsules, gels, creams, emulsions, patches or the like.

Hydrophilic Esters

The phenolic hydroxyl of capsaicin, a capsaicinoid, or other TRPV1 agonist, may be esterified with a polyhydroxylated functional group to impart significant aqueous solubility while impairing its ability to interact with a TRPV1 receptor. The ester group may be a short chain alcohol or polyol or alternately may be a long chain derivative with sufficient metabolic or hydrolytic instability to allow the liberation of capsaicin in vivo. An example of a long chain ester derivative is a polyethylene glycol conjugate of capsaicin which may be formed by covalent linkage of a hydrolyzable linker group. One such functionalized polyethylene glycol is succinate terminated PEG or PEG having an activated terminal carboxyl group. These derivatives can form an activated ester with the phenolic hydroxyl of capsaicin. Other terminally carboxylated PEG derivatives include direct carboxymethylation of PEG containing one or more methylene groups and glutarate.

PEGylated capsaicin, capsaicinoid, or other TRPV1 agonist, may have higher aqueous solubility and provide a controlled delivery of capsaicin to local tissue by direct administration to the site of action. The PEG conjugate ester hydrolyzes upon administration liberating capsaicin directly to the site of action. This results in localized delivery of capsaicin, a capsaicinoid, or other TRPV1 agonist to the surrounding tissues, minimizing potential systemic exposure.

The physical and chemical properties of the hydrophilic esters described here may also be modified to control the rate of hydrolysis, pharmacokinetics and pharmacodynamics. Improvements in formulations, for example, by using liposomes, may be possible with polyethylene glycol-conjugated capsaicin.

PEGylation of capsaicin may reduce binding of capsaicin to the TRPV1 receptor due to steric hindrance of the PEG chain by occupying the phenolic hydroxyl of capsaicin which has been shown to be a required element of receptor site binding. In order for capsaicin to induce pharmacological action, the PEG moiety must first be hydrolyzed to liberate free capsaicin. Therefore, the pungency and toxicity associated with free capsaicin is not incurred prior to metabolic activation.

Gemini Dimers

Delivery and administration of capsaicin, a capsaicinoid, or other TRPV1 agonist to a target tissue may be significantly modified by conversion to a novel prodrug by covalently linking the phenolic hydroxyl groups through a carbonyl bridge and is independent of structure of R2 and R3. The structure show below represents the dimers of this type:

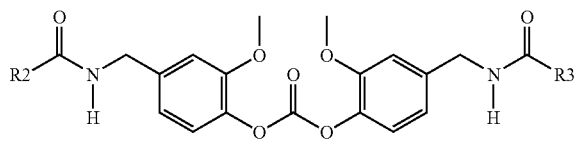

where R2 and R3 are independently selected from the group consisting of a substituted or unsubstituted, saturated or unsaturated, linear or branched, $C_1$-$C_{20}$ alkyl. In both R2 and R3, when the alkyl group is unsaturated, each unsaturated bond may either be in the cis or trans configuration, independent of other unsaturated bonds. In some variations, either R2 alone or both R2 and R3 are (3E)-2-methyloct-3-ene or (3Z)-2-methyloct-3-ene or n-octane.

A duplex gemini dimer of naltrexone showed rapid hydrolysis in an in vitro study, delivering only the monomer to the receptor fluid (see: Hammell D C, Hamad M, Vaddi H K, Crooks P A, Stinchcomb A L. A duplex "Gemini" prodrug of naltrexone for transdermal delivery. J Control Release. 2004. 97(2):283-90). In vitro permeation data suggested that external application of the dimer to human skin provided a 2-fold higher level of naltrexone in the receptor fluid. A capsaicin gemini dimer has been made following the same synthetic procedure of reacting two capsaicin molecules through the phenolic hydroxyls with phosgene to produce the duplex gemini dimer of capsaicin. This molecule may also demonstrate improved dermal uptake and subsequent hydrolysis in the skin to liberate free capsaicin.

As noted above, gemini dimers of TRPV1 agonists may also result in delayed or reduced pungency. As free access of the hydroxyl group is required for TRPV1 binding, such compounds are expected to be pharmacologically inactive at the TRPV1 receptor until such time as the dimer linkage is hydrolyzed.

Mutual Prodrugs

One other aspect of this invention is the dual prodrug possibility of simultaneously delivering two active agents such as l-menthol (or any other active agent) and capsaicin (or any other suitable TRPV1 agonist). For example, l-Menthol is used as a topical or local analgesic agent and is a selective agonist of the cold receptor, also known as TRPM8. See: Jordt S E, McKemy D D, Julius D. Lessons from peppers and peppermint: the molecular logic of thermosensation. Curr Opin Neurobiol. 2003. 13(4):487-492. In many chronic pain syndromes, simultaneous activation of C-fibers with a TRPV1 agonist and Aδ-fibers with a TRPM8 agonist is predicted to produce less pain during the process of nociceptor desensitization. See: Anand P. Capsaicin and menthol in the treatment of itch and pain: recently cloned receptors provide the key. Gut. 2003. 52(9):1233-5. The capsaicin and l-menthol prodrug is shown below:

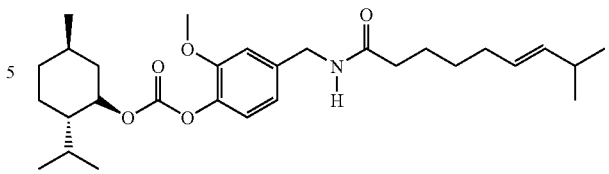

Along with Helicobacter Pylori infection, excessive acid secretion in the stomach, reduction in gastric mucosal blood flow, ethanol, smoking and stress, excessive use of COX inhibitors to treat pain and inflammation is thought responsible for gastric erosion and ulcer formation. It is also sometimes perceived that excessive capsaicin consumption can promote gastric ulcers in view of the potential irritancy produced by TRPV1 agonists. In fact, patients with ulcers are often advised either to limit or avoid capsaicin consumption. However, investigations carried out in recent years have revealed that capsaicin does not stimulate but actually inhibits acid secretion, stimulates alkali mucus secretions, and stimulates gastric mucosal blood flow. Capsaicin acts by stimulating afferent neurons in the stomach and signals for protection against injury-causing agents. Epidemiologic surveys suggest that gastric ulcers are more common in populations which report low chili pepper consumption. All of these factors support the notion that capsaicin or other TRPV1 agonists should actually help prevent and heal ulcers. See, Satyanarayana M N. Capsaicin and gastric ulcers. Crit Rev Food Sci Nutr. 2006. 46(4):275-328. Accordingly, mutual prodrugs of capsaicin and a COX inhibitor may display lower rates of gastric erosion than COX inhibitors alone. By way of example and not limitation, a mutual prodrug of capsaicin and naproxen is shown below:

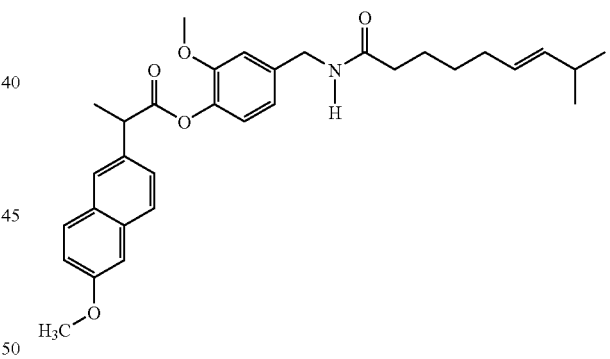

Mutual prodrugs of capsaicin and COX inhibitors may display reduced gastrointestinal irritation and damage, particularly with chronic dosing. Similar observations have been made with mutual prodrugs of COX inhibitors combined with histamine receptor antagonists (Fukuhara A, Imai T, Otagiri M. Stereoselective disposition of flurbiprofen from a mutual prodrug with a histamine H2-antagonist to reduce gastrointestinal lesions in the rat. Chirality. 1996. 8(7):494-502).

In addition, evidence exists that local or topical administration of gabapentin may be useful for pain management (Carlton S M, Zhou S. Attenuation of formalin-induced nociceptive behaviors following local peripheral injection of gabapentin. Pain. 1998. 76(1-2):201-207.) Accordingly, topical gabapentin is available at a number of compounding pharmacies in the US (e.g., http://www.drugsandthings.com/Pain Management.html#Shingles%20Formula). Thus the combination of gabapentin or pregabalin with capsaicin (or any other TRPV1 agonist) may display unique utility in the treatment of chronic pain syndromes. By way of example and not limitation, a capsaicin and gabapentin mutual prodrug is shown below:

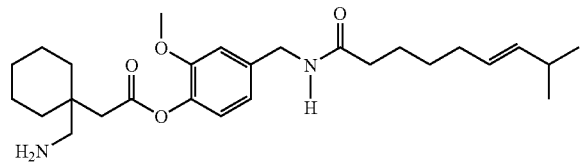

II. Formulations

The TRPV1 agonists described here can be administered by oral, parenteral (intra-muscular, intraperitoneal, intravenous, or subcutaneous injection), topical (either passively or using iontophoresis, or sonophoresis or electroporation), transmucosal (e.g., nasal, vaginal, rectal, or sublingual), pulmonary (e.g., via dry powder inhalation) or oral routes of administration or using bioerodable inserts and can be formulated in dosage forms appropriate for each route of administration.

Topical

The TRPV1 agonists described above may be used for topical administration where the targeted site of action is cutaneous nociceptors found in the dermis and/or epidermis. Thus, creams, gels, patches or ointments may be prepared with pharmaceutical excipients including thickening agents and penetration enhancers intended for topical administration. Compositions may, e.g., range from about 0.01 to about 20% by weight of the TRPV1 agonist. Exemplary penetration enhancers that may be useful for use with the formulations described here include, but are not limited to: d-pipertone and oleic acid; l-menthone and oleic acid; l-menthone and ethyl oleate; l-menthone and benzyl alcohol; ethylene glycol and l-menthone; benzyl alcohol and oleyl alcoholic; l-menthone and cetyl alcohol; 1,3-butanediol and oleic acid; diethylene glycol monoethyl ether and l-menthone; ethelyne glycol and oleic acid; isopropyl myristate; oleyl alcohol and 1-3, butandiol; l-menthone and isopropyl butyrate; l-menthone and 1,3-butanediol; n-hexane and oleic acid; menthone and methanol; methylnonenoic acid and n-hexane; oleyl alcohol and propylene glycol; methylnonenoic alcohol and dimethylacetamide, stearyl alcohol, oleyl alcohol, linoleyl alcohol, linolenyl alcohol, caprylic alcohol, decyl alcohol, lauryl alcohol, propylene glycol, polyethylene glycol, ethylene glycol, diethylene glycol, triethylene glycol, ethoxy digkycol, dipropylene glycol, glycerol, propanediol, butanediol, pentanediol, hexanetriol 2-lauryl alcohol, myristyl alcohol, cetyl alcohol, capric acid, lauric acid, myristic acid, stearic acid, oleic acid, caprylic acid, valeric acid, heptanoic acid, pelagonic acid, caproic acid, isovaleric acid, neopentanoic acid, trimethyl hexanoic acid, neodecanoic acid, isostearic acid, neoheptanoic acid, neononanoic acid, isopropyl n-decanoate, isopropyl palmitate, octyldodecyl myristate, ethyl acetate, butyl acetate, methyl acetate, isopropyl n-butyrate, ethylvalerate, methylpropionate, diethyl sebacate, ethyl oleate, isopropyl n-hexanoate, isopropyl myristate, urea, dimethylacetamide, diethyltoluamide, dimethylformamide, dimethyloctamide, dimethyldecamide, 1-hexyl-4-methoxycarbonyl-2-pyrrolidone, 1-lauryl-4-carboxy-2-pyrrolidone, 1-methyl-4-carboxy-2-pyrrolidone, 1-alkyl-4-imidazolin-2-one, 1-methyl-2-pyrrolidone, 2-pyrrolidone, 1-lauryl-2-pyrrolidone, 1-hexyl-4-carboxy-2-pyrrolidone, 1-methyl-4-methoxycarbonyl-2-pyrrolidone, 1-lauryl-4-methoxycarbonyl-2-pyrrolidone, dimethylsulfoxide, decylmethylsulfoxide, N-cocoalkypyrrolidone, N-dimethylaminopropylpyrrolidone, N-tallowalkylpyrrolidone, N-cyclohexylpyrrolidone, 1-farnesylazacycloheptan-2-one, 1-geranylgeranylazacycloheptan-2-one, fatty acid esters of -(2-hydroxyethyl)-2-pyrrolidone, 1-geranylazacycloheptan-2-one, 1-dodecylazacycloheptane-2-one (Azone®), 1-(3,7-dimethyloctyl)azacycloheptan-2-one, 1-geranylazacyclohexane-2-one, 1-(3,7,11-trimethyldodecyl)azacyclohaptan-2-one, 1-geranylazacyclopentan-2,5-dione, 1-farnesylazacyclopentan-2-one, benzyl alcohol, butanol, pentanol, hexanol, octanol, nonanol, decanol, ethanol, 2-butanol, 2-pentanol, propanol, diethanolamine, triethanolamine; hexamethylenelauramide and its derivatives, benzalkonium chloride, sodium laurate, sodium lauryl sulfate; cetylpyridinium chloride, citric acid, succinic acid, salicylic acid. sylicylate Cetyltrimethyl ammonium bromide, tetradecyltrimethylammonium bromide; octadecyltrimethylammonium chloride; dodecyltrimethylammonium chloride, hexadecyltrimethylammonium chloride, Span 20, Span 40, Span 60, Span 80, Span 85, Poloxamer 231, Poloxamer 182, Poloxamer 184), Brij 30, Brij 35, Brij 93, Brij 96, Span 99, Myrj 45, Myrj 51, Myrj 52, Miglyol 840, glycholic, sodium salts of taurocholic, lecithin, sodium cholate, desoxycholic acids, D-limonene, α-pinene, β-carene, α-terpineol, terpinen-4-ol, carvol, carvone, pulegone, piperitone, Ylang ylang, menthone, anise, chenopodium, eucalyptus, limonene oxide, α-pinene oxide, cyclopentene oxide, 1,8-cineole, cyclohexene oxide, N-heptane, N-octane, N-nonane, N-decane, N-undecane, N-dodecane, N-tridecane, N-tetradecane, N-hexadecane, essential oils (e.g., tea tree oils), and mixtures of any of the above.

Ointments typically contain a conventional ointment base selected from the four recognized classes: oleaginous bases; emulsifiable bases; emulsion bases; and water-soluble bases. Lotions are preparations to be applied to the skin or mucosal surface without friction, and are typically liquid or semiliquid preparations in which solid particles, including the active agent, are present in a water or alcohol base. Lotions are usually suspensions of solids, and preferably, for the present purpose, comprise a liquid emulsion of the oil-in-water type. Creams, as known in the art, are viscous liquid or semisolid emulsions, either oil-in-water or water-in-oil. Topical formulations may also be in the form of a gel, e.g., a semisolid, suspension-type system, or in the form of a solution. Yet another form of topical application can be a patch. Patches are of various types such as microreservoir, monolithic, or liquid reservoir. All of these types of patches can be prepared with the molecules of this invention as one of the active ingredients.

Parenteral

Capsaicin, capsaicinoids, and most TRPV1 agonists are poorly soluble in aqueous solutions. Described here are prodrugs of these molecules, which have been prepared to impart improved aqueous solubility, in addition to other advantageous properties. These compounds may be formulated in suitable aqueous suspensions or solutions intended for intravenous or intramuscular injection, or for direct instillation into sites of pain, inflammation, and/or disease (e.g., arthritic joints). Formulations may include suitable buffers and stabilizing excipients optionally with water, saline, or other sterile medium for injection.

Preparations according to this invention for parenteral administration include sterile aqueous and non-aqueous solutions, suspensions, or emulsions. Examples of non-aqueous solvents or vehicles are propylene glycol polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating or by heating.

Patches

The TRPV1 agonists described above may be formulated in patches. Patch designs may include drug in adhesive matrix, micro-liquid reservoir or multilayered liquid reservoir. The aliphatic prodrugs may exist in the oil form as a preferred state. These substances may be formulated directly in patches where they may form microreservoirs. Other compositions may include nano- or microparticulate suspensions in an adhesive matrix.

Oral

The capsaicin, capsaincinoids and TRPV1 agonist compounds described here may also be delivered orally, and the oral formulations may include enteric coatings. Alteration of physicochemical properties such as lipophilicity or Hydrophilic Lipophilic Balance ("HLB") may be tailored to optimize tissue uptake thereby improving the bioavailability of derivatized forms.

Solid dosage forms for oral administration include capsules, tablets, pills, powders, and granules. In such solid dosage forms, the active compound is typically admixed with at least one inert pharmaceutically acceptable carrier such as sucrose, lactose, or starch. Such dosage forms can also comprise, as is normal practice, additional substances other than inert diluents, e.g., lubricating, agents such as magnesium stearate. In the case of capsules, tablets, and pills, the dosage forms may also comprise buffering agents. As noted above, tablets and pills can additionally be prepared with enteric coatings.

Liquid dosage forms for oral administration include pharmaceutically acceptable emulsions, solutions, suspensions, syrups, optionally with elixirs containing inert diluents commonly used in the art, such as water. In addition to such inert diluents, the liquid dosage forms described here can also include adjuvants, such as wetting agents, emulsifying and suspending agents, and sweetening, flavoring, and perfuming agent Mucosal Similar to oral bioavailability, mucosal delivery methods may demonstrate improved performance for administrations such as bladder instillation or oral mucositis. These formulations may include creams, gels, ointments or oil/water emulsions. Compositions for rectal or vaginal administration are preferably suppositories, which may contain, in addition to the active substance, excipients such as cocoa butter or a suppository wax. Compositions for nasal or sublingual administration may also be prepared with standard excipients well known in the art.

III. Methods of Use

Methods for treating pain and other medical conditions are also described. In general, these methods comprise the step of dermally, transdermally, locally or systemically delivering compounds and prodrugs (i.e., the TRPV1 agonists) previously described to treat any one of a variety of medical conditions or ailments. In some variations, the unwanted condition is pain. For example, the pain may be associated with postherpetic neuralgia, diabetic neuropathy, HIV-associated neuropathy, complex regional pain syndrome, cancer, nerve injury, cancer chemotherapy, vulvodynia, trauma, surgery, chronic musculoskeletal pain, lower back pain, osteoarthritis or rheumatoid arthritis. In other variations, the conditions to be treated include, but are not limited to, psoriasis, pruritis, itch, cancer, prostatic hypertrophy, wrinkles, sinusitis, rhinitis, alopecia, or hirsutism.

The dosage of active ingredient in the compositions of this invention may be varied depending on the dosage form used. However, in all instances, the amount of the active ingredient shall be such that a suitable dosage form is obtained. The selected dosage depends upon the desired therapeutic effect, on the route of administration, and on the duration of the treatment desired. Generally, dosage levels of between 0.001 to 30 mg/kg of body weight daily are administered to mammals.

The following examples are for illustrative purposes only, and are not intended to be limiting of the scope of the appended claims.

IV. EXAMPLES

Example 1

Synthesis of (4-[(((6E)-8-methylnon-6-enoylamino) methyl]-2-methoxyphenyl formate)

Preparation (4-[(((6E)-8-methylnon-6-enoylamino)methyl]-2-methoxyphenyl formate):

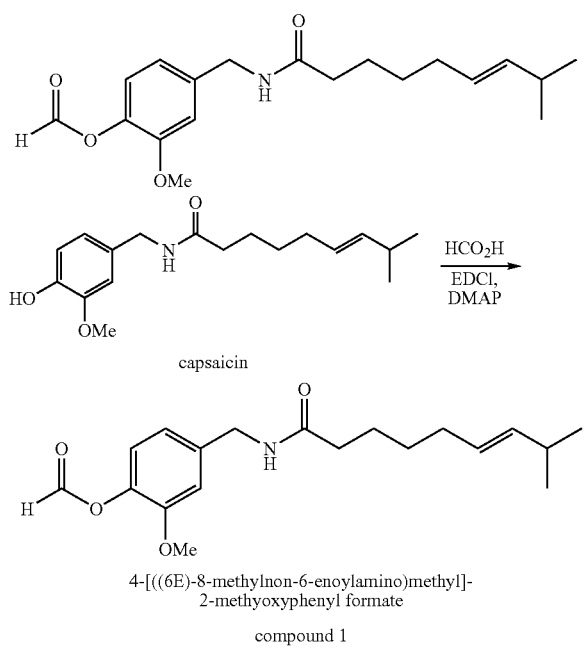

Figure 2:
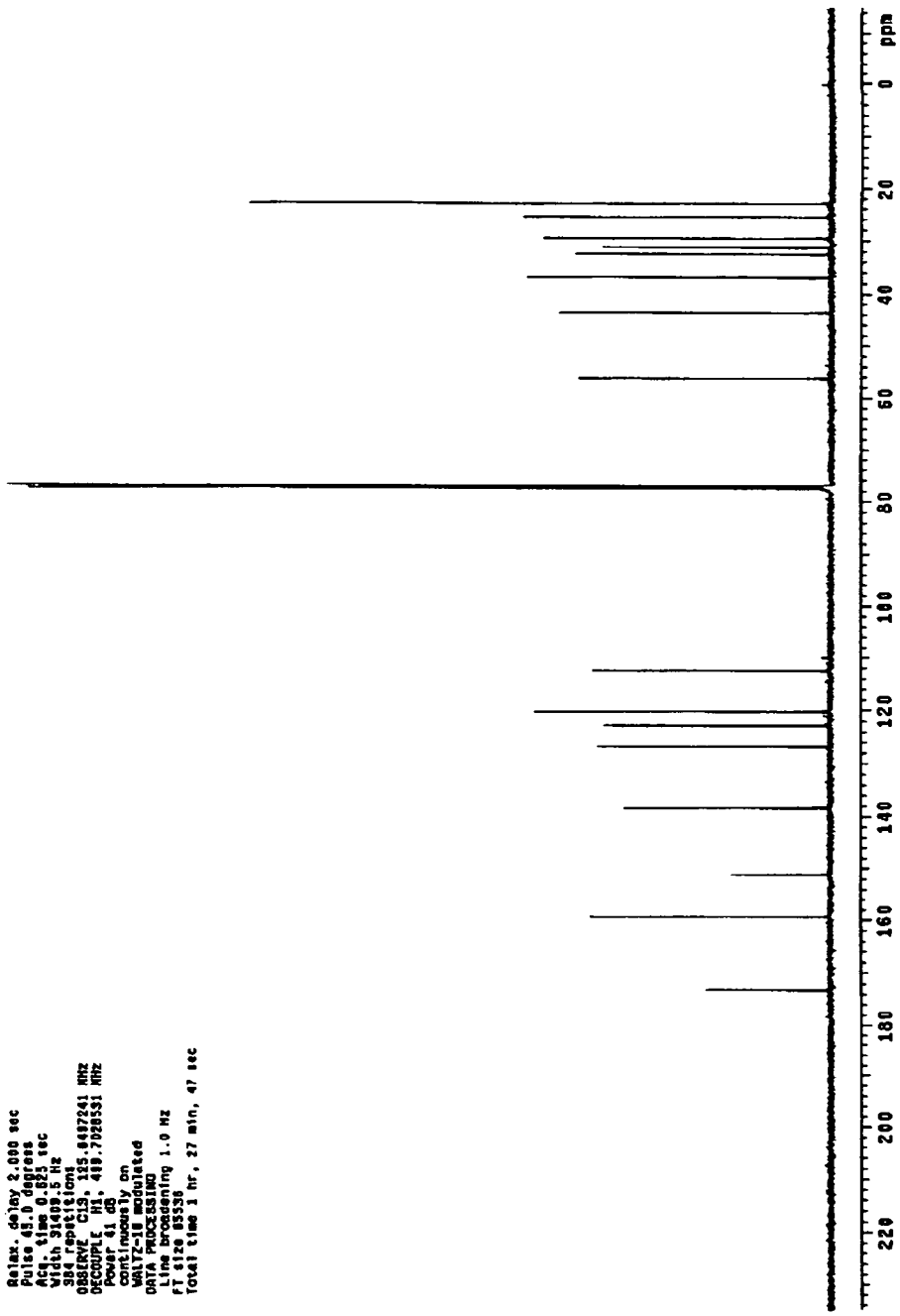
FIG. 2 provides a $^{13}$C-NMR of 4-[((6E)-8-methylnon-6-enoylamino)methyl]-2-methyoxyphenyl formate.
Figure 3:
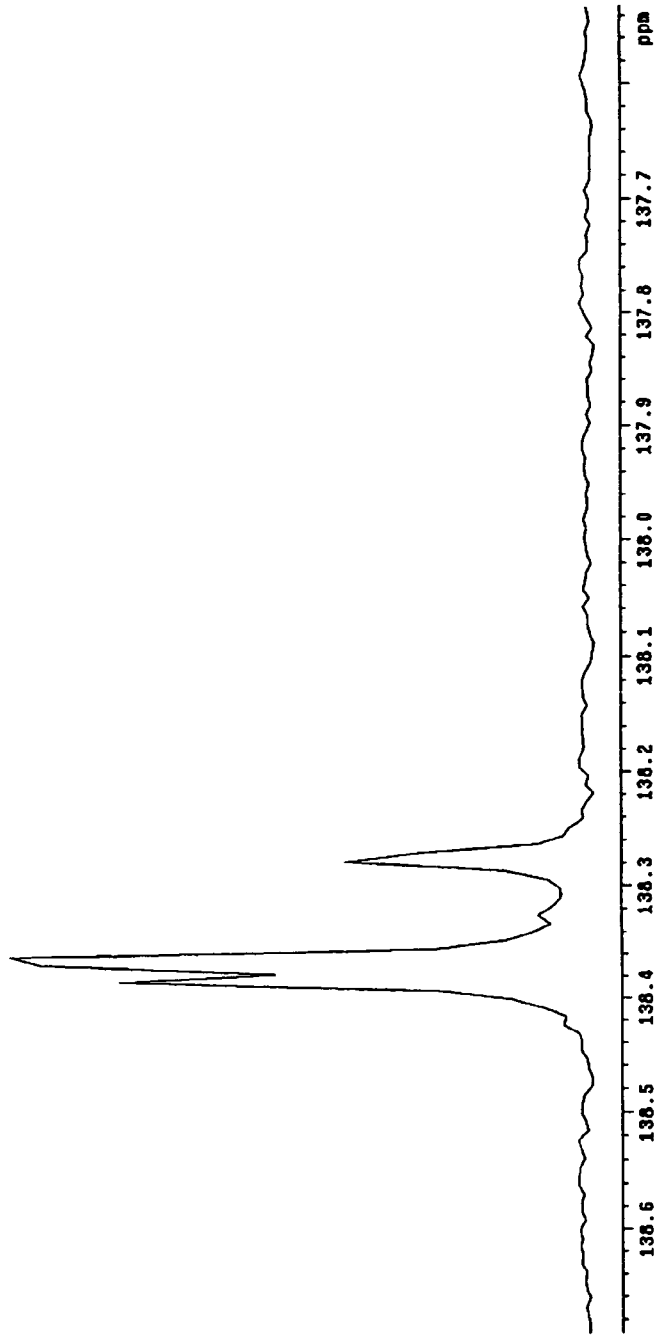
FIG. 3 provides a $^{13}$C-NMR of 4-[((6E)-8-methylnon-6-enoylamino)methyl]-2-methyoxyphenyl formate (expanded).
Figure 4:
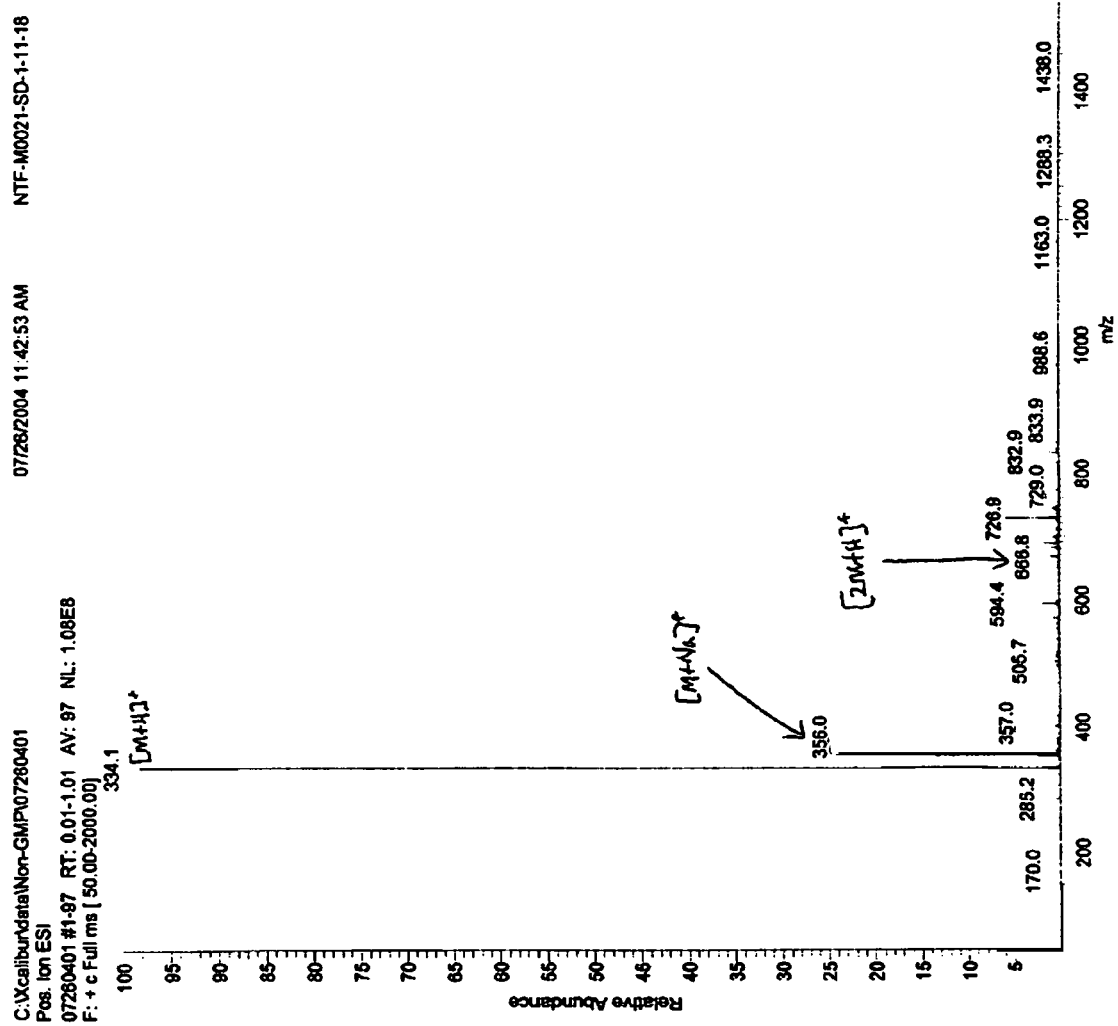
FIG. 4 is a mass spectrum of 4-[((6E)-8-methylnon-6-enoylamino)methyl]-2-methyoxyphenyl formate.
Figure 5:
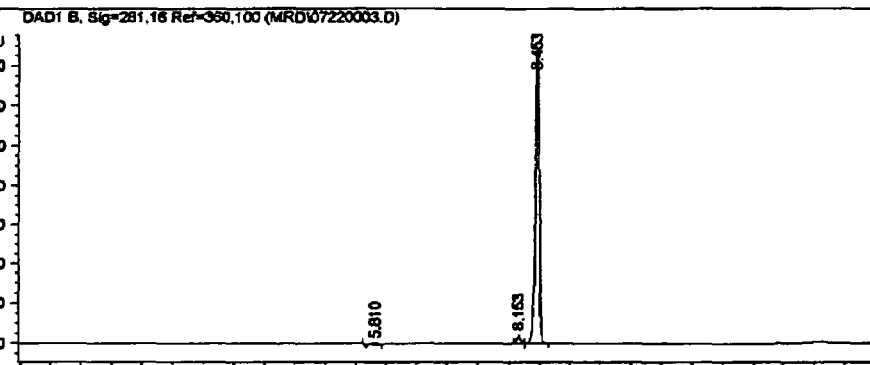
FIG. 5 is an HPLC analysis of 4-[((6E)-8-methylnon-6-enoylamino)methyl]-2-methyoxyphenyl formate.

Formic acid (0.53 mL, 13.8 mmol; Aldrich) and 1-(3-dimethylaminopropyl)-3-ethylcarbodiimide hydrochloride (EDCI) (2.26 g, 11.8 mmol; BACHEM), followed with DMAP (180 mg; Aldrich) was added to a solution of capsaicin (1.2 g, 3.93 mmol; Torcan Chemical LTD) in anhydrous dichloromethane (20 mL; Aldrich). The reaction mixture was stirred under nitrogen for 4 hours, and diluted with more dichloromethane (Fisher Scientific), washed with brine (Fisher Scientific), dried over MgSO$_4$ (Spectrum), and concentrated to dryness. The obtained crude product was subjected to a silica gel column (Sorbent). The column was eluted with 30% ethyl acetate (Fisher Scientific) in hexane (Fisher Scientific). 1.3 g of product was obtained as clear oil, however, NMR of this product indicated about 5-6% percent of capsaicin was present. Therefore, this product was resubjected to the above reaction condition. Subsequently, 1.05 g of 4-[((6E)-8-methylnon-6-enoylamino)methyl]-2-methyoxyphenyl formate was obtained as clear oil in 80.2% yield. $^1$H-NMR and $^{13}$C-NMR were consistent with the desired structure (see FIGS. 1, 2 and 3). Mass spectral analysis of the product was consistent with the desired structure (see FIG. 4). HPLC analysis of the product showed 96.7% (AUC) purity (see FIG. 5). Elemental analysis (FIG. 6) of the product indicated that a small amount of water was probably adsorbed in the product.

Calculated for $C_{19}H_{27}NO_4$: C, 68.44; H, 8.16; N, 4.20. Found: C, 67.93; H, 8.21; N, 4.20.

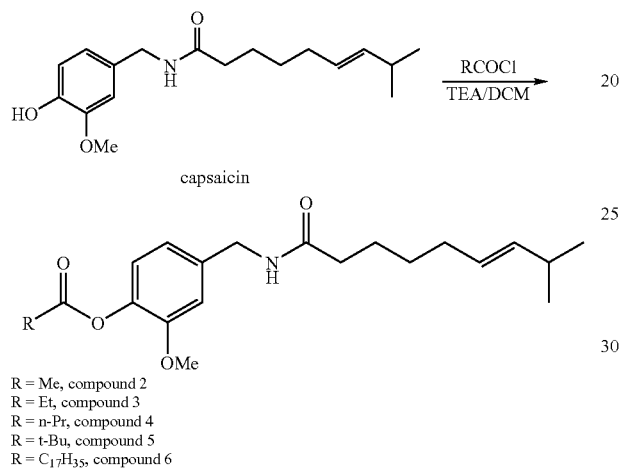

R = Me, compound 2
R = Et, compound 3
R = n-Pr, compound 4
R = t-Bu, compound 5
R = $C_{17}H_{35}$, compound 6

Example 2

Synthesis of (4-[((6E)-8-methylnon-6-enoylamino)methyl]-2-methyoxyphenyl acetate)

Preparation of (4-[((6E)-8-methylnon-6-enoylamino)methyl]-2-methyoxyphenyl acetate):

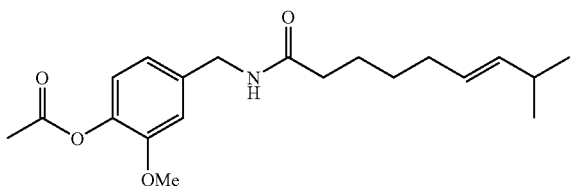

A solution of capsaicin (1 equivalent) in 15 mL of dichloromethane was cooled by ice-bath. To this acid chloride (1.5 equivalent; Aldrich), followed with triethylamine (2 equivalents; Aldrich) was added. The reaction mixture was stirred for 1 hour, and then warmed up to room temperature for another hour. The reaction mixture was diluted with more dichloromethane, washed with brine, followed by diluted aqueous HCl solution (Fisher Scientific), brine, saturated aqueous NaHCO$_3$ solution (Aldrich), and brine successively, dried over MgSO$_4$, and concentrated to dryness. The obtained crude product was subjected to a silica gel column chromatography (30% ethyl acetate in hexane as the eluent).

Figure 7:
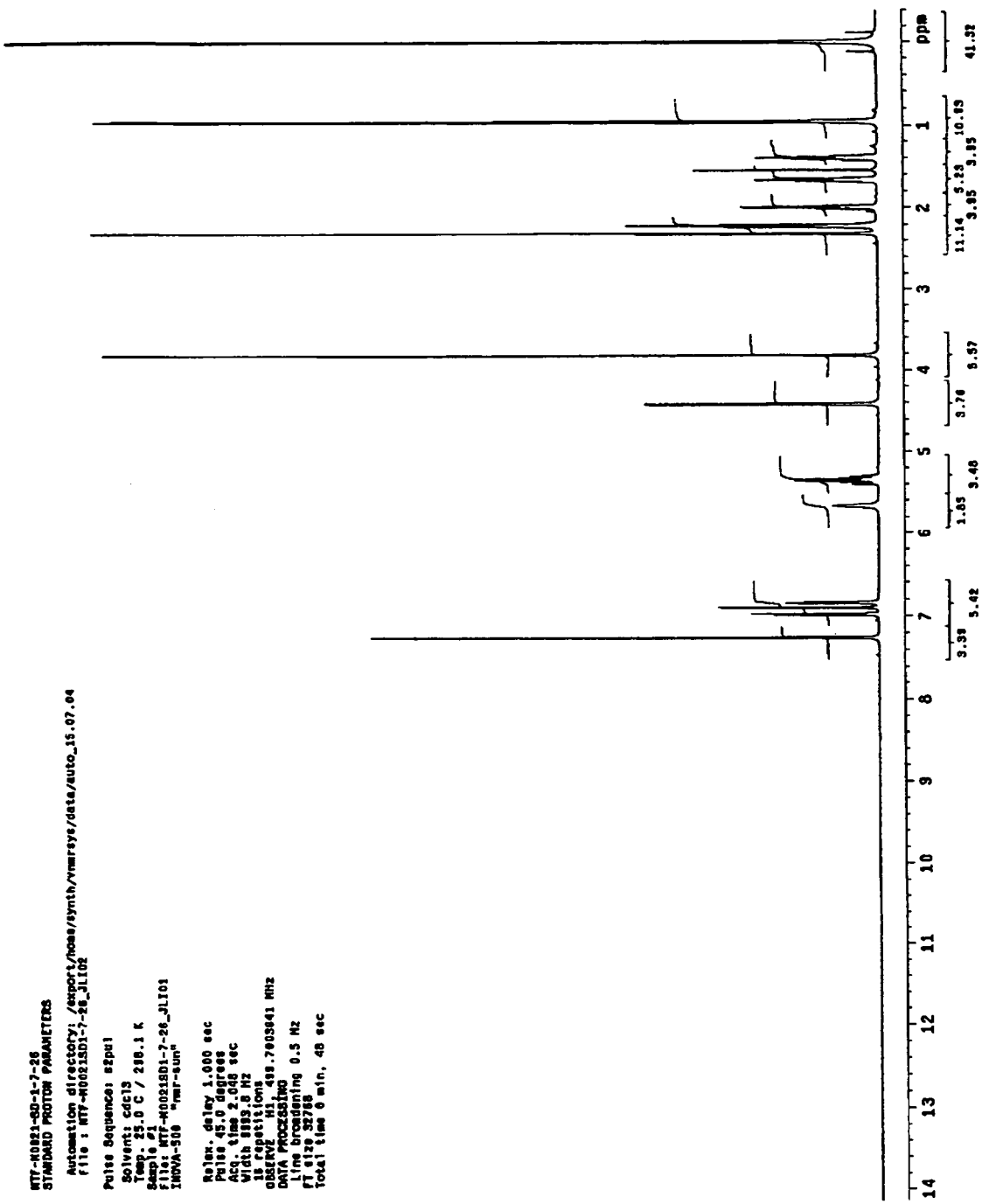
FIG. 7 provides a $^1$H-NMR of 4-[((6E)-8-methylnon-6-enoylamino)methyl]-2-methyoxyphenyl acetate.
Figure 8:
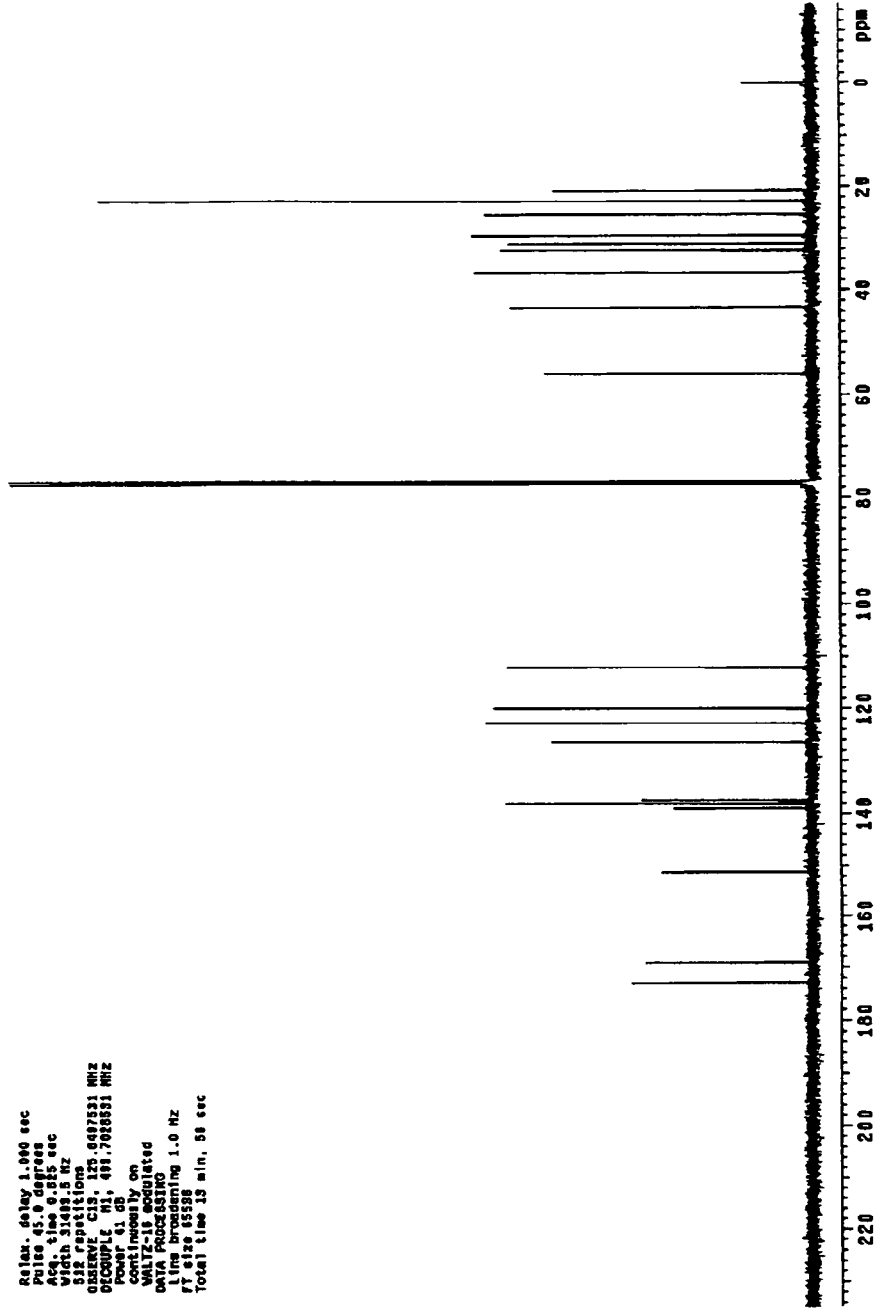
FIG. 8 provides a $^{13}$C-NMR of 4-[((6E)-8-methylnon-6-enoylamino)methyl]-2-methyoxyphenyl acetate.
Figure 9:
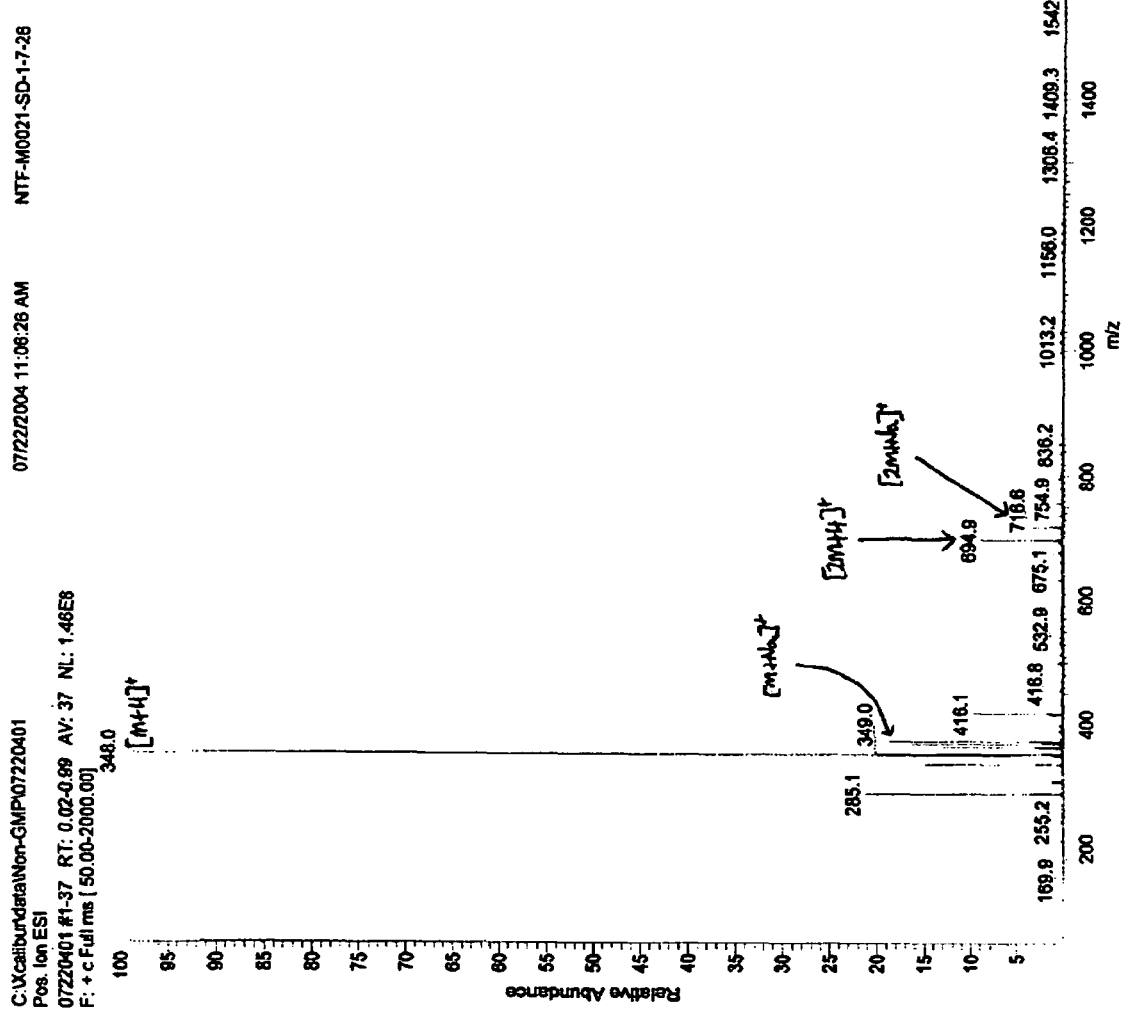
FIG. 9 is a mass spectrum of 4-[((6E)-8-methylnon-6-enoylamino)methyl]-2-methyoxyphenyl acetate.
Figure 10:
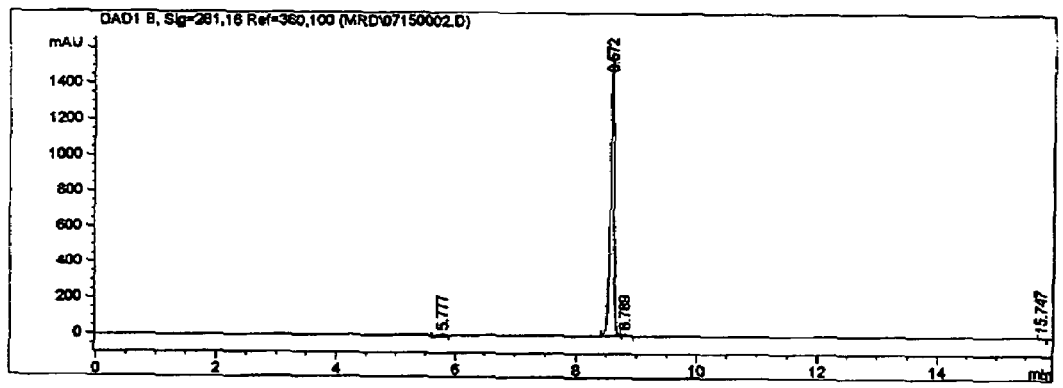
FIG. 10 is an HPLC analysis of 4-[((6E)-8-methylnon-6-enoylamino)methyl]-2-methyoxyphenyl acetate.
Figure 11:
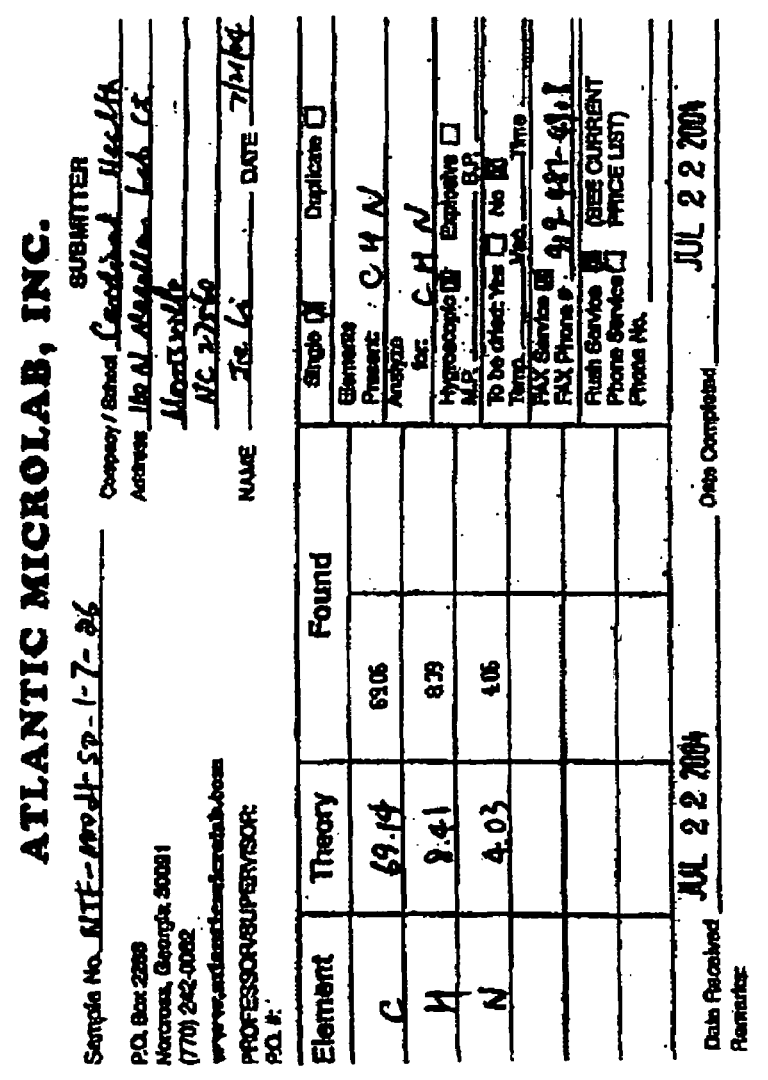

After the chromatography, 1.0 g of the product was obtained as white solid. The obtained product was further triturated with hexane to give 0.94 g of 4-[((6E)-8-methylnon-6-enoylamino)methyl]-2-methyoxyphenyl acetate in 86.0% yield as white solid. $^1$H-NMR and $^{13}$C-NMR were consistent with the desired structure (FIGS. 7 and 8). Mass spectral analysis of the product was consistent with the desired structure (FIG. 9). HPLC analysis of the product showed 98.0% (AUC) purity (FIG. 10). Elemental analysis (FIG. 11) of the product was also consistent with the desired structure: Calculated for $C_{20}H_{29}NO_4$: C, 69.14; H, 8.41; N, 4.03. Found: C, 69.06; H, 8.39; N, 4.06.

Example 3

Synthesis of (4-[((6E)-8-methylnon-6-enoylamino)methyl]-2-methyoxyphenyl propanoate)

Preparation of (4-[((6E)-8-methylnon-6-enoylamino)methyl]-2-methyoxyphenyl propanoate):

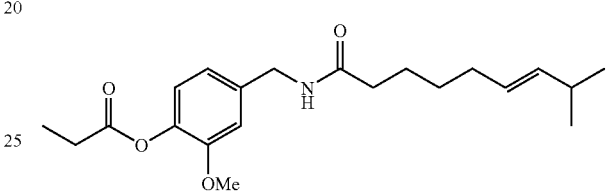

A solution of capsaicin (1 equivalent) in 15 mL of dichloromethane was cooled by ice-bath. Acid chloride (1.5 equivalent; Aldrich), followed with triethylamine (2 equivalents; Aldrich) was added to this solution. The reaction mixture& was stirred for 1 hour, and then warmed up to room temperature for another hour. The reaction mixture was diluted with more dichloromethane, washed with brine, followed by diluted aqueous HCl solution (Fisher Scientific), brine, saturated aqueous NaHCO$_3$ solution (Aldrich), and brine successively, dried over MgSO$_4$, and concentrated to dryness. The obtained crude product was subjected to a silica gel column chromatography (30% ethyl acetate in hexane as the eluent).

Figure 12:
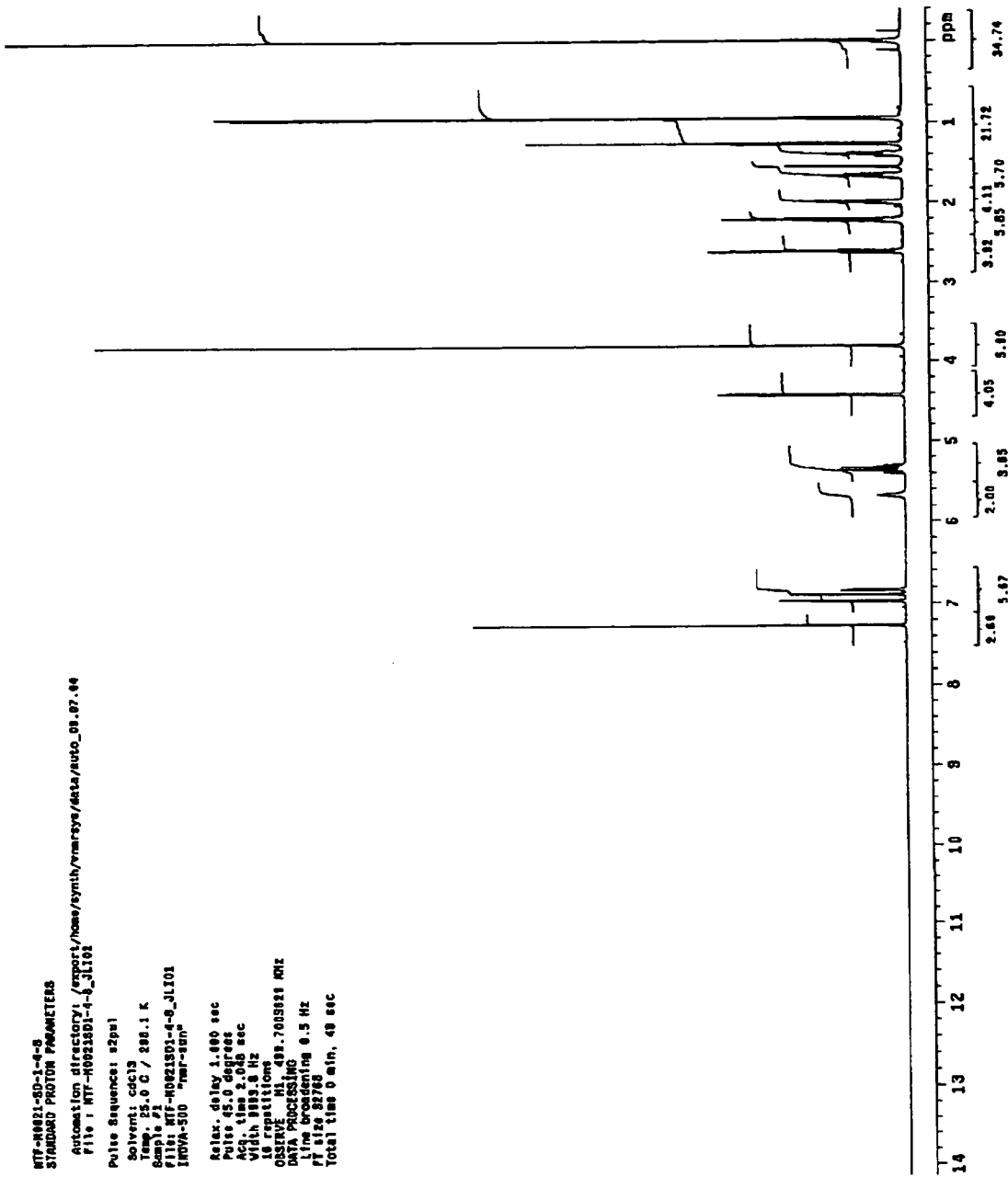
FIG. 12 provides a $^1$H-NMR of 4-[((6E)-8-methylnon-6-enoylamino)methyl]-2-methyoxyphenyl propanoate.
Figure 13:
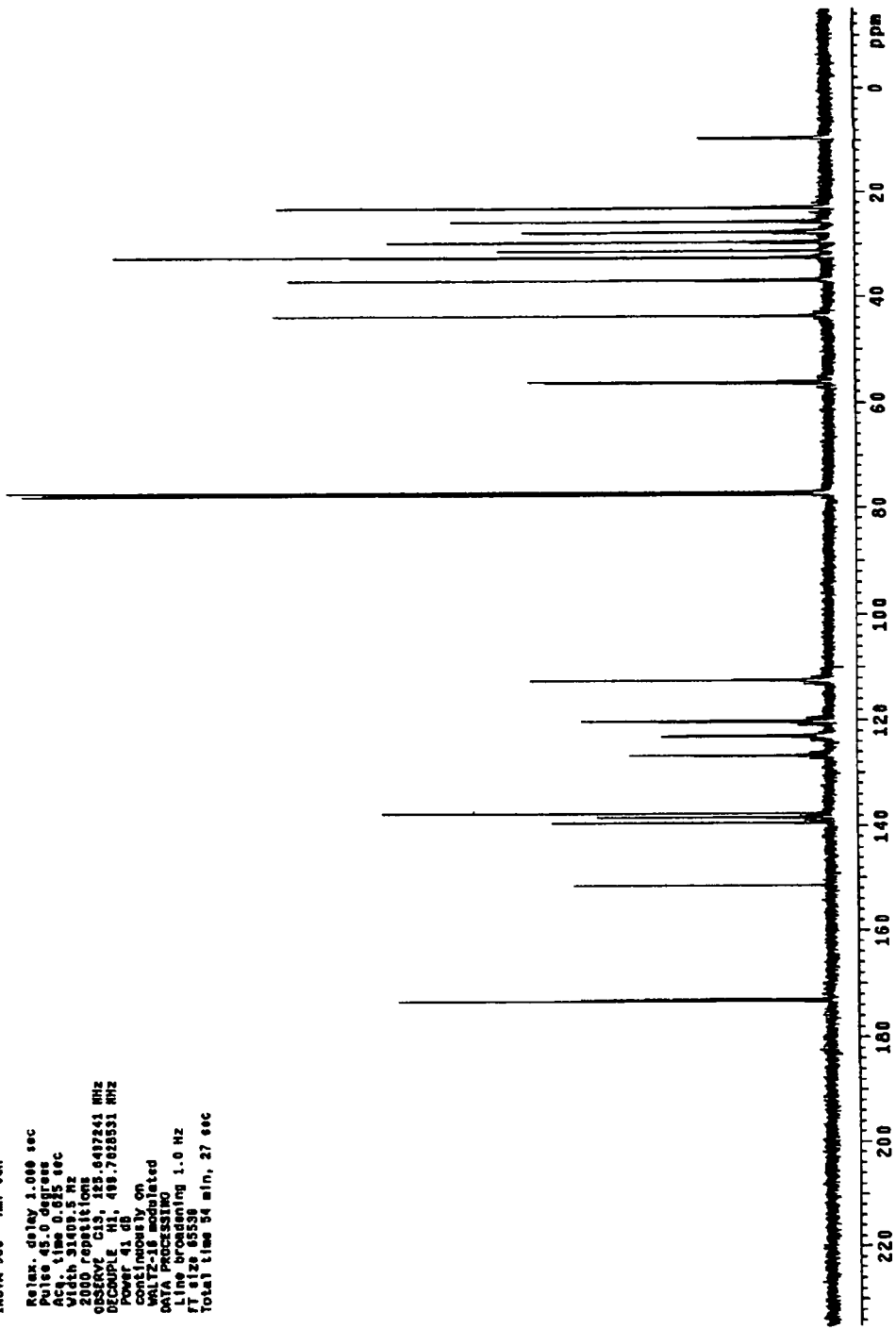
FIG. 13 provides a $^{13}$C-NMR of 4-[((6E)-8-methylnon-6-enoylamino)methyl]-2-methyoxyphenyl propanoate.
Figure 14:
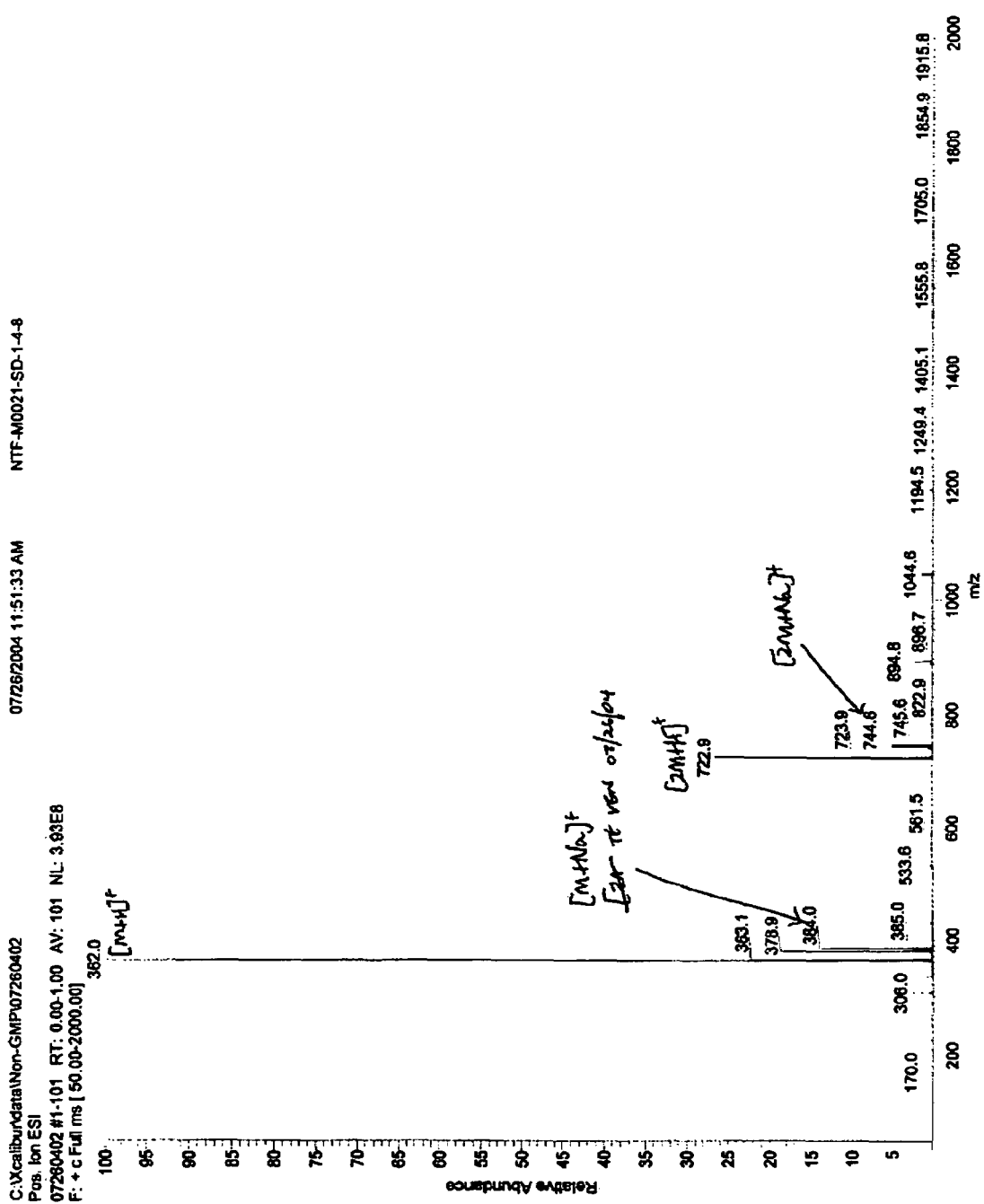
FIG. 14 is a mass spectrum of 4-[((6E)-8-methylnon-6-enoylamino)methyl]-2-methyoxyphenyl propanoate.

After the chromatography, 1.09 g of 4-[((6E)-8-methylnon-6-enoylamino)methyl]-2-methyoxyphenyl propanoate was obtained in 94.0% yield as pale yellow oil. $^1$H-NMR and $^{13}$C-NMR were consistent with the desired structure (FIGS. 12 and 13). Mass spectral analysis of the product was consistent with the desired structure (FIG. 14). HPLC analysis of the product showed 99.6% (AUC) purity (FIG. 15). Elemental analysis (FIG. 16) of the product was also consistent with the desired structure: Calculated for $C_{21}H_{31}NO_4$: C, 69.78; H, 8.64; N, 3.87. Found: C, 69.56; H, 8.74; N, 3.92.

Example 4

Synthesis of (4-[((6E)-8-methylnon-6-enoylamino)methyl]-2-methoxyphenyl butanoate)

Preparation of (4-[((6E)-8-methylnon-6-enoylamino)methyl]-2-methyoxyphenyl butanoate):

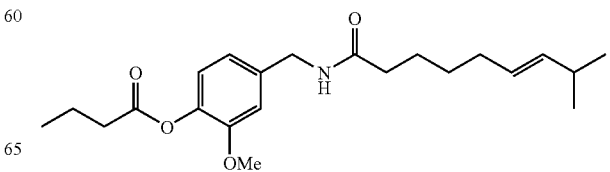

A solution of capsaicin (1 equivalent) in 15 mL of dichloromethane was cooled by ice-bath. To this acid chloride (1.5 equivalent; Aldrich), followed with triethylamine (2 equivalents; Aldrich) was added. The reaction mixture was stirred for 1 hour, and then warmed up to room temperature for another hour. The reaction mixture was diluted with more dichloromethane, washed with brine, followed by diluted aqueous HCl solution (Fisher Scientific), brine, saturated aqueous NaHCO$_3$ solution (Aldrich), and brine successively, dried over MgSO$_4$, and concentrated to dryness. The obtained crude product was subjected to a silica gel column chromatography (30% ethyl acetate in hexane as the eluent).

A solution of capsaicin (1 equivalent) in 15 mL of dichloromethane was cooled by ice-bath. To this added the acid chloride (1.5 equivalent), followed with triethylamine (2 equivalents). The reaction mixture was stirred for 1 hour, and then warmed up to room temperature for another hour. The reaction mixture was diluted with more dichloromethane, washed with brine, followed by diluted aqueous HCl solution, brine, saturated aqueous NaHCO$_3$ solution, and brine successively, dried over MgSO$_4$, and concentrated to dryness. The obtained crude product was subjected to a silica gel column chromatography (30% ethyl acetate in hexane as the eluent).

Figure 17:
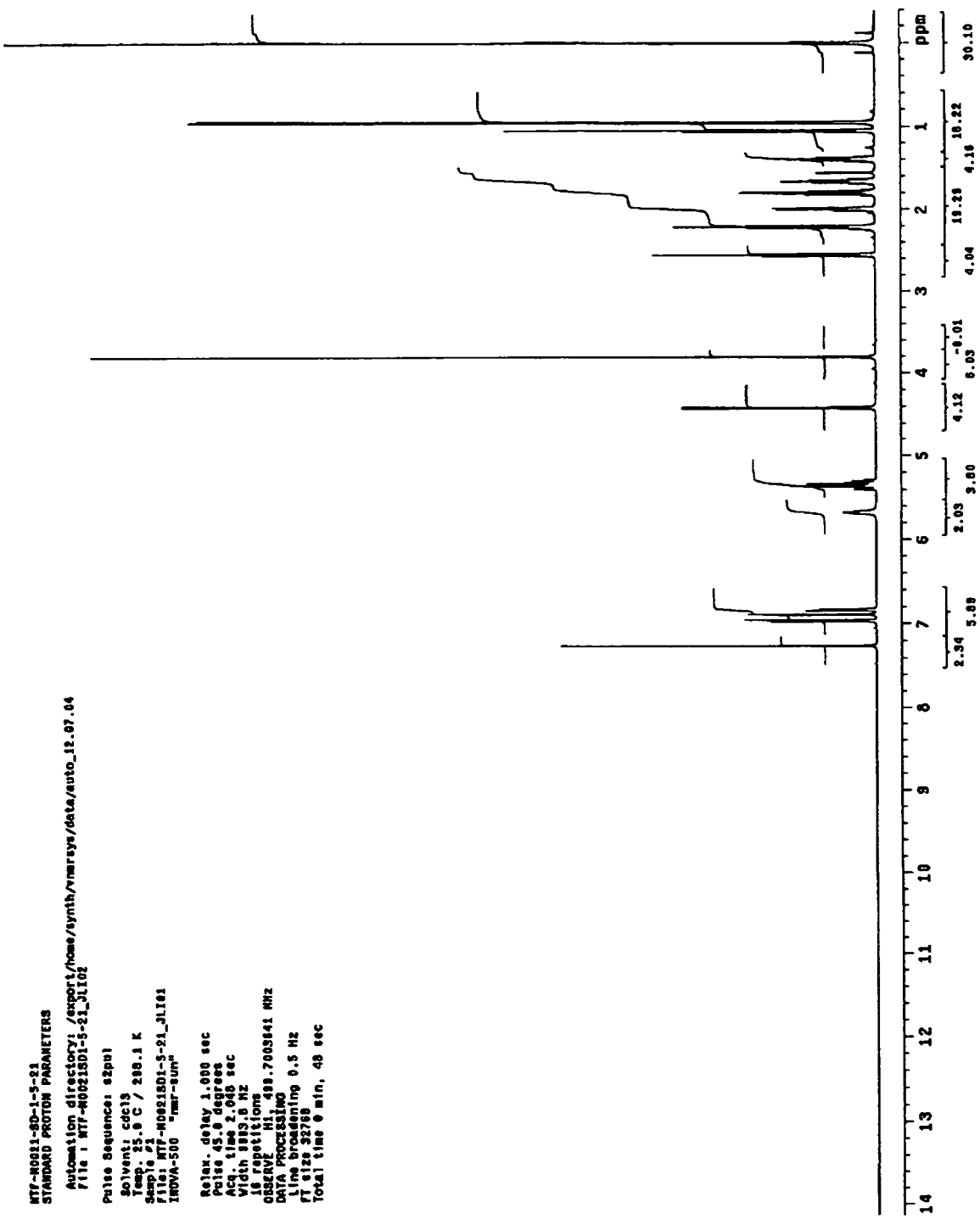
FIG. 17 provides a $^1$H-NMR of 4-[((6E)-8-methylnon-6-enoylamino)methyl]-2-methyoxyphenyl butanoate.
Figure 18:
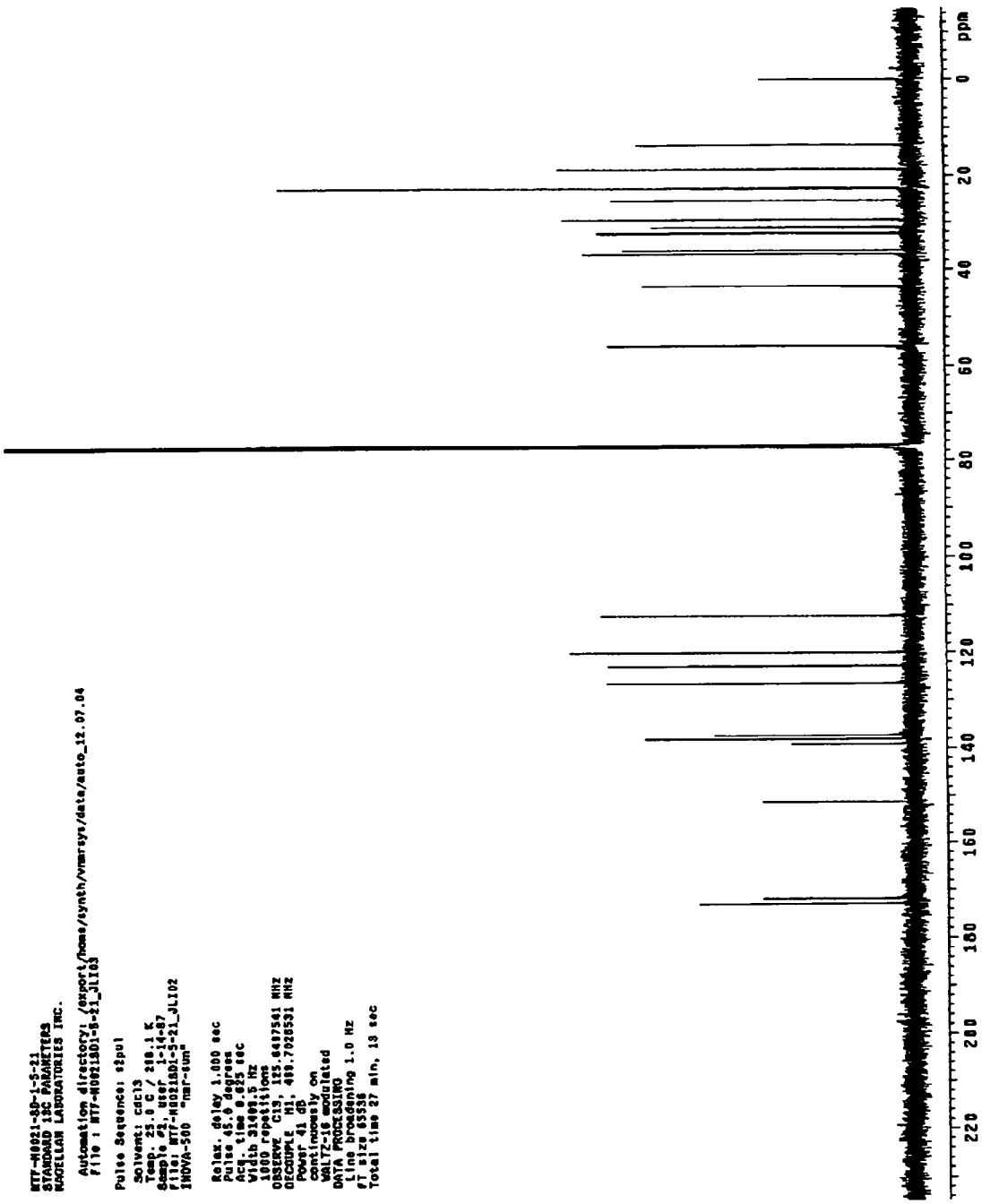
FIG. 18 provides a $^{13}$C-NMR of 4-[((6E)-8-methylnon-6-enoylamino)methyl]-2-methyoxyphenyl butanoate.
Figure 19:
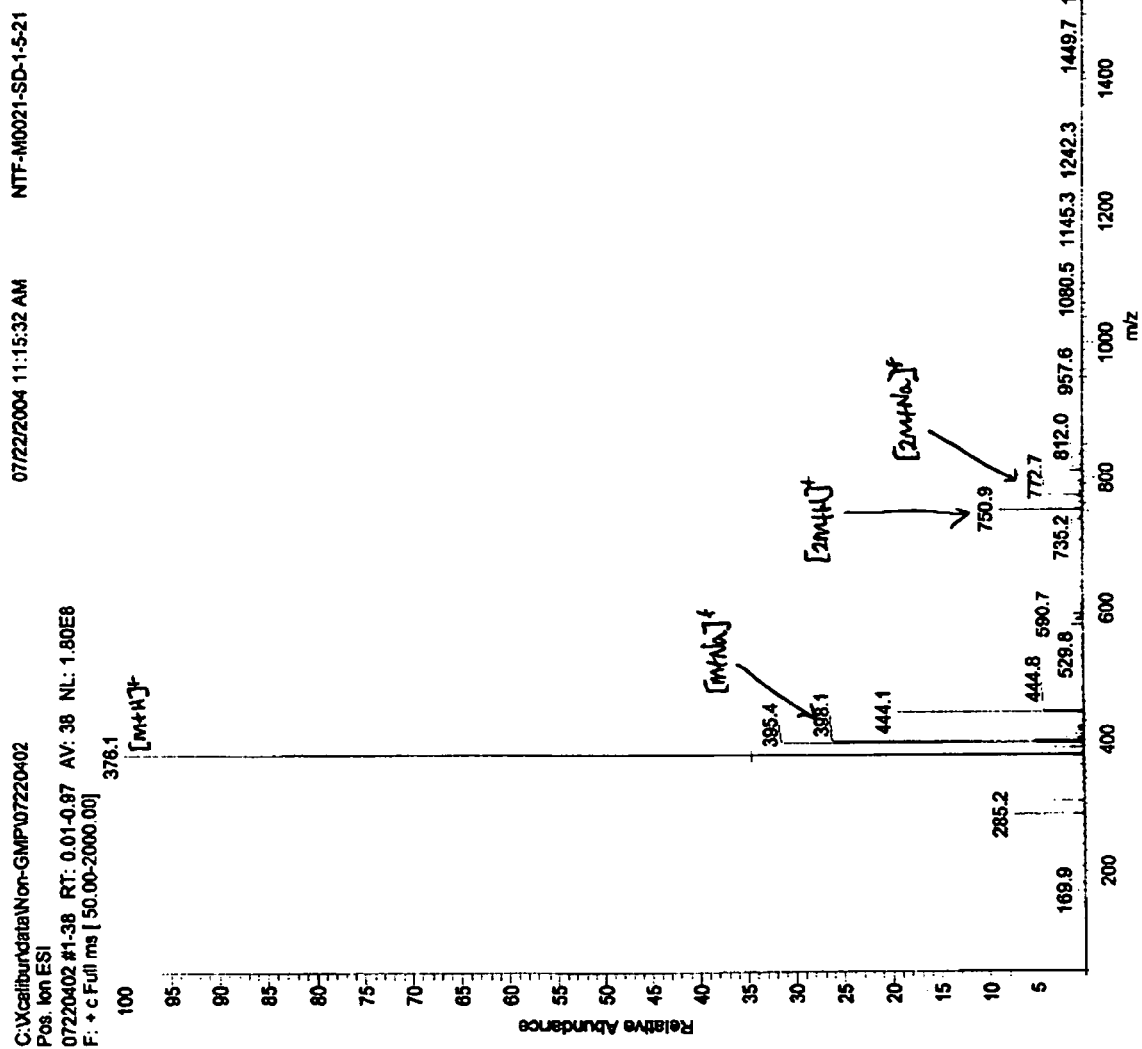
FIG. 19 is a mass spectrum of 4-[((6E)-8-methylnon-6-enoylamino)methyl]-2-methyoxyphenyl butanoate.

After the chromatography, 1.18 g of 4-[((6E)-8-methyl-non-6-enoylamino)methyl]-2-methyoxyphenyl butanoate was obtained in 96.0% yield as white solid. $^1$H-NMR and $^{13}$C-NMR were consistent with the desired structure (FIGS. 17 and 18). Mass spectral analysis of the product was consistent with the desired structure (FIG. 19). HPLC analysis of the product showed 98.9% (AUC) purity (FIG. 20). Elemental analysis (FIG. 21) of the product was also consistent with the desired structure: Calculated for C$_{22}$H$_{33}$NO$_4$: C, 70.37; H, 8.86; N, 3.73. Found: C, 70.29; H, 8.90; N, 3.75.

Example 5

Synthesis of (4-[((6E)-8-methylnon-6-enoylamino) methyl]-2-methoxyphenyl 2,2-dimethylpropanoate)

Preparation of (4-[((6E)-8-methylnon-6-enoylamino)methyl]-2-methyoxyphenyl 2,2-dimethylpropanoate):

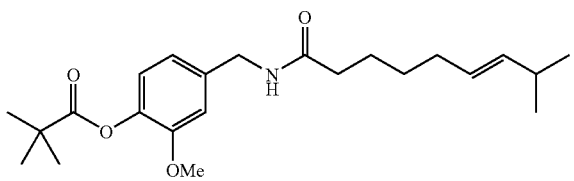

A solution of capsaicin (1 equivalent) in 15 mL of dichloromethane was cooled by ice-bath. To this acid chloride (1.5 equivalent; Aldrich), followed with triethylamine (2 equivalents; Aldrich) was added. The reaction mixture was stirred for 1 hour, and then warmed up to room temperature for another hour. The reaction mixture was diluted with more dichloromethane, washed with brine, followed by diluted aqueous HCl solution (Fisher Scientific), brine, saturated aqueous NaHCO$_3$ solution (Aldrich), and brine successively, dried over MgSO$_4$, and concentrated to dryness. The obtained crude product Was subjected to a silica gel column chromatography (30% ethyl acetate in hexane as the eluent).

A solution of capsaicin (1 equivalent) in 15 mL of dichloromethane was cooled by ice-bath. To this added the acid chloride (1.5 equivalent), followed with triethylamine (2 equivalents). The reaction mixture was stirred for 1 hour, and then warmed up to room temperature for another hour. The reaction mixture was diluted with more dichloromethane, washed with brine, followed by diluted aqueous HCl solution, brine, saturated aqueous NaHCO$_3$ solution, and brine successively, dried over MgSO$_4$, and concentrated to dryness. The obtained crude product was subjected to a silica gel column chromatography (30% ethyl acetate in hexane as the eluent).

Figure 22:
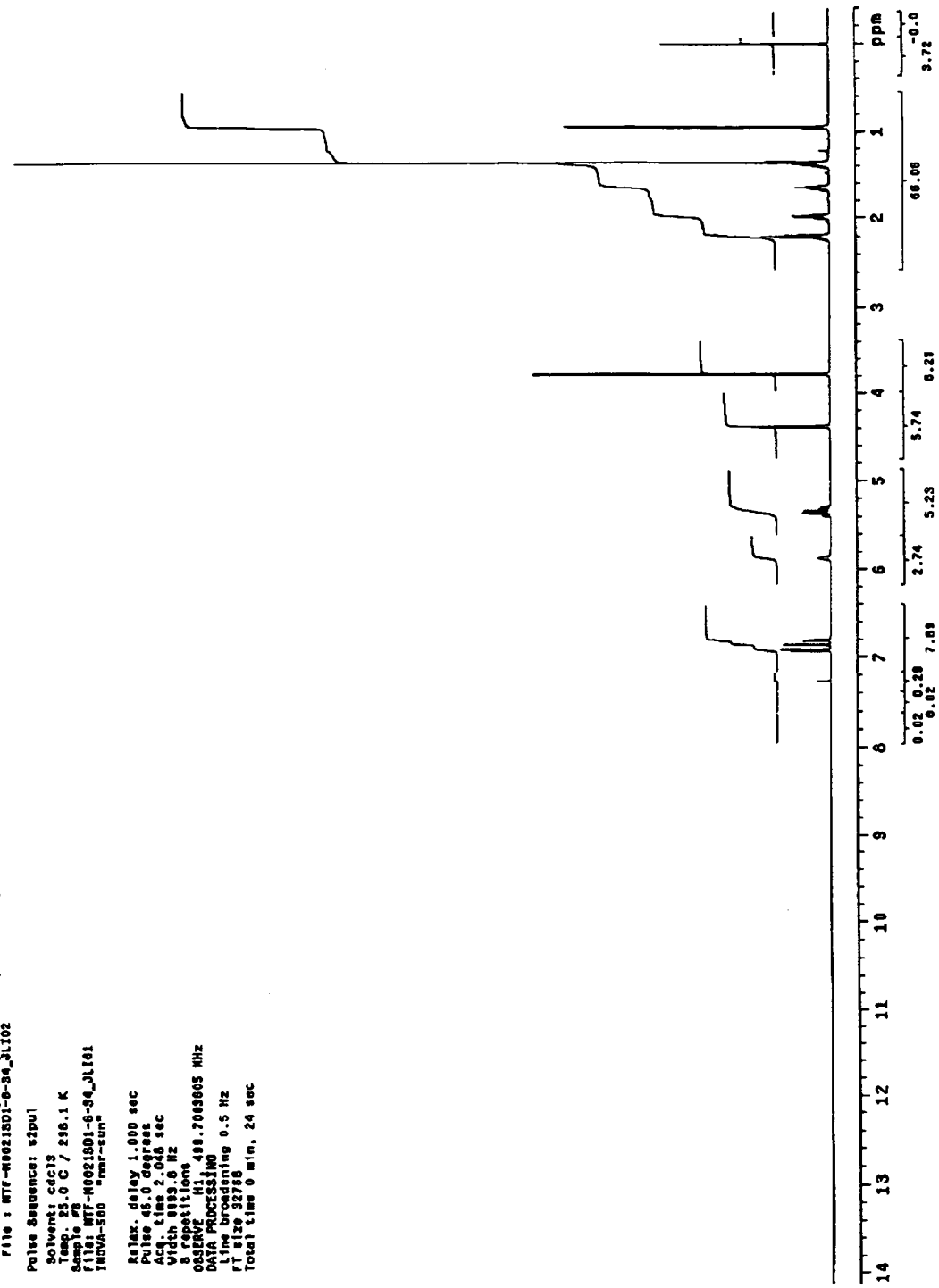
FIG. 22 provides a $^1$H-NMR of 4-[((6E)-8-methylnon-6-enoylamino)methyl]-2-methyoxyphenyl 2,2-dimethylpropanoate.
Figure 23:
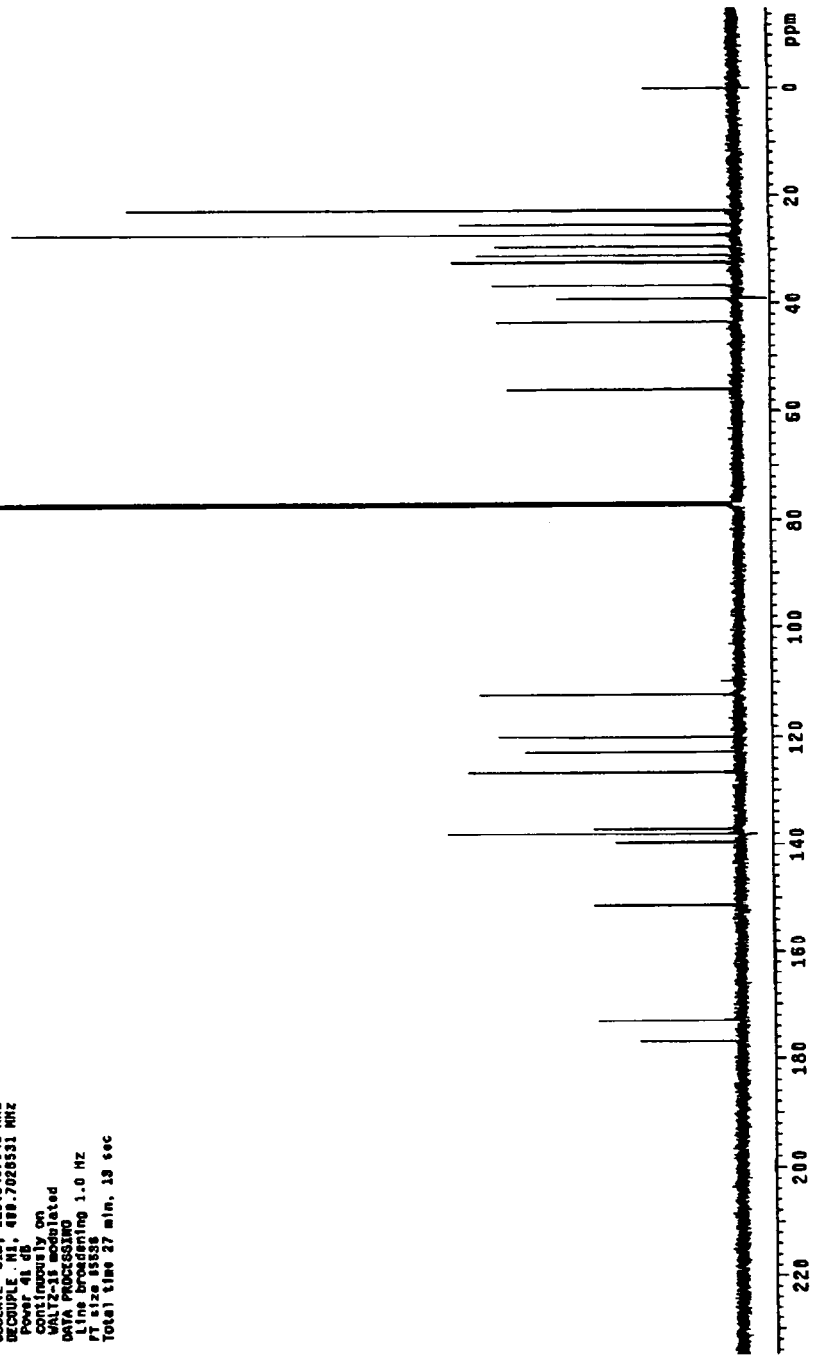
FIG. 23 provides a $^{13}$C-NMR of 4-[((6E)-8-methylnon-6-enoylamino)methyl]-2-methyoxyphenyl 2,2-dimethylpropanoate.
Figure 24:
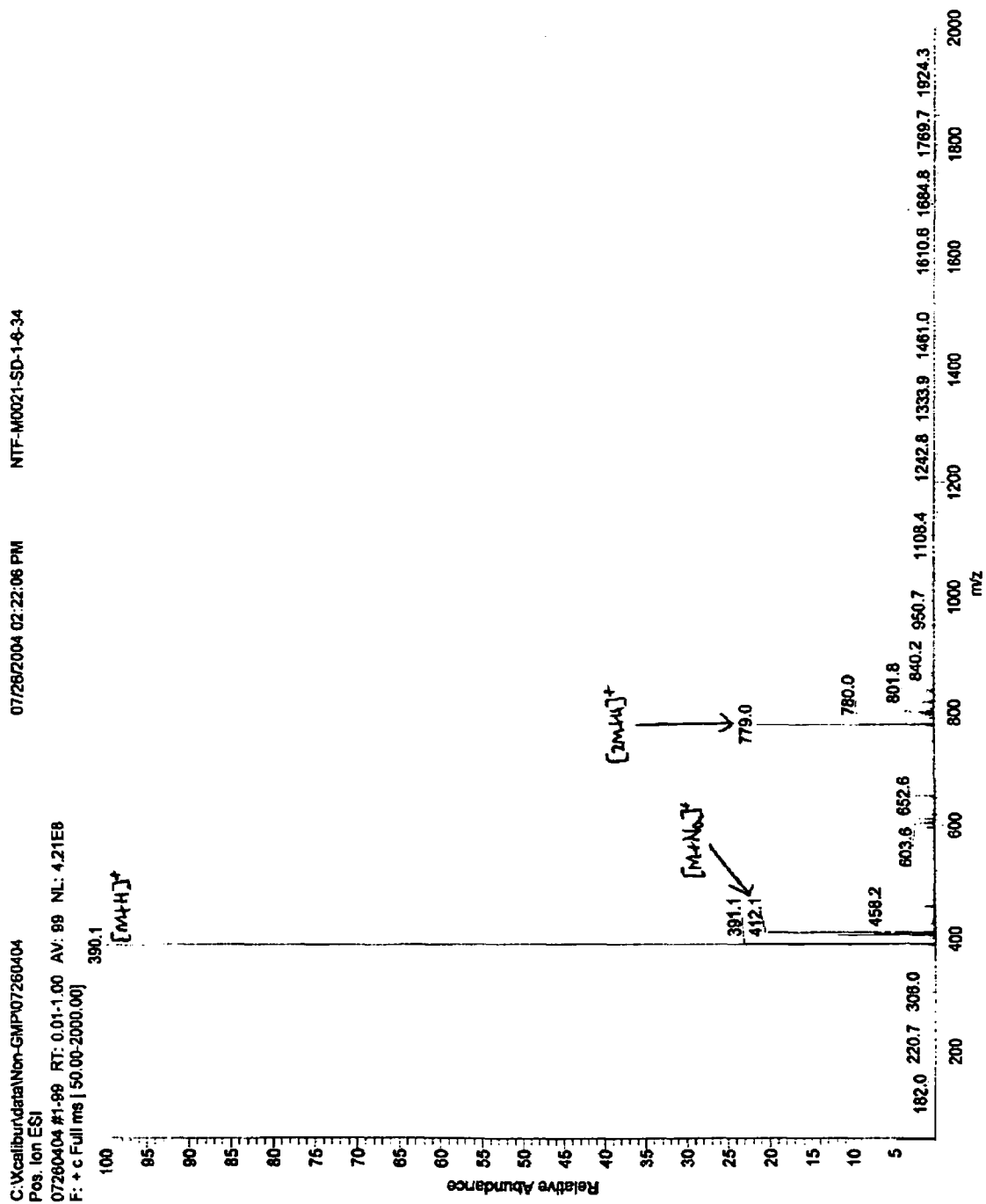
FIG. 24 is a mass spectrum of 4-[((6E)-8-methylnon-6-enoylamino)methyl]-2-methyoxyphenyl 2,2-dimethylpropanoate.

After the chromatography, 1.18 g of 4-[((6E)-8-methyl-non-6-enoylamino)methyl]-2-methoxyphenyl 2,2-dimethylpropanoate was obtained in 92.5% yield as clear oil. $^1$H-NMR and $^{13}$C-NMR were consistent with the desired structure (FIGS. 22 and 23). Mass spectral analysis of the product was consistent with the desired structure (FIG. 24). HPLC analysis of the product showed 99.6% (AUC) purity (FIG. 25). Elemental analysis (FIG. 26) of the product was also consistent with the desired structure: Calculated for C$_{23}$H$_{35}$NO$_4$: C, 70.92; H, 9.06; N, 3.60. Found: C, 70.63; H, 9.22; N, 3.65.

Example 6

Synthesis of (4-[((6E)-8-methylnon-6-enoylamino) methyl]-2-methyoxyphenyl octadecanoate)

Preparation of (4-[((6E)-8-methylnon-6-enoylamino)methyl]-2-methyoxyphenyl octadecanoate):

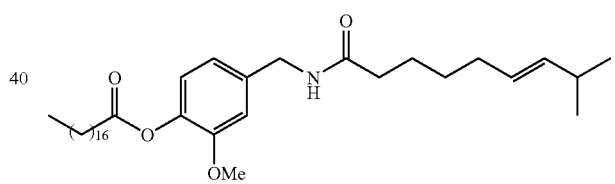

A solution of capsaicin (1 equivalent) in 15 mL of dichloromethane was cooled by ice-bath. Acid chloride (1.5 equivalent; Aldrich), followed with triethylamine (2 equivalents; Aldrich) was added to this solution. The reaction mixture was stirred for 1 hour, and then warmed up to room temperature for another hour. The reaction mixture was diluted with more dichloromethane, washed with brine, followed by diluted aqueous HCl solution (Fisher Scientific), brine, saturated aqueous NaHCO$_3$ solution (Aldrich), and brine successively, dried over MgSO$_4$, and concentrated to dryness. The obtained crude product was subjected to a silica gel column chromatography (30% ethyl acetate in hexane as the eluent).

A solution of capsaicin (1 equivalent) in 15 mL of dichloromethane was cooled by ice-bath. To this added the acid chloride (1.5 equivalent), followed with triethylamine (2 equivalents). The reaction mixture was stirred for 1 hour, and then warmed up to room temperature for another hour. The reaction mixture was diluted with more dichloromethane, washed with brine, followed by diluted aqueous HCl solution, brine, saturated aqueous NaHCO$_3$ solution, and brine successively, dried over MgSO$_4$, and concentrated to dryness. The obtained crude product was subjected to a silica gel column chromatography (30% ethyl acetate in hexane as the eluent).

Figure 27:
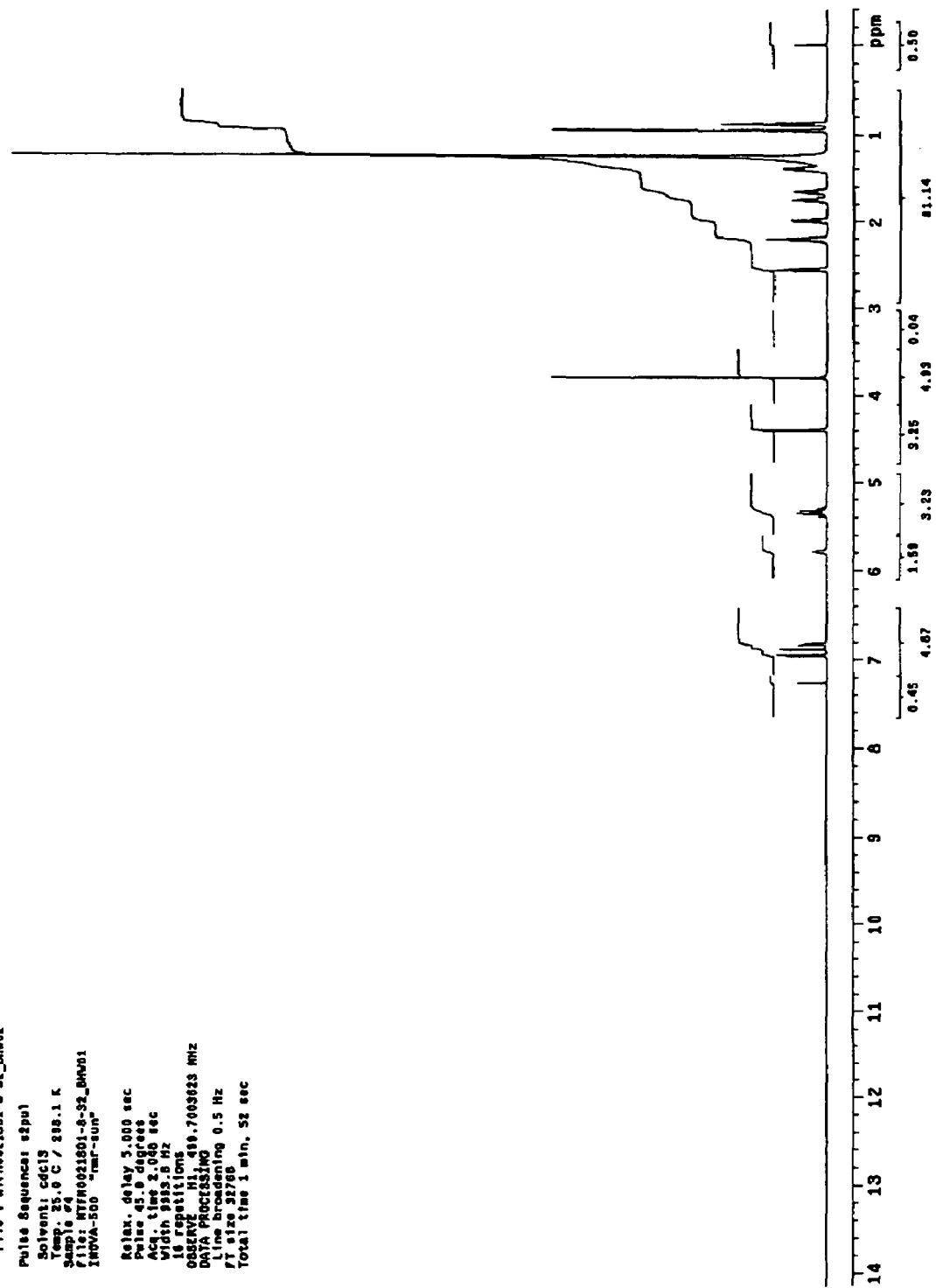
FIG. 27 provides a $^1$H-NMR of 4-[((6E)-8-methylnon-6-enoylamino)methyl]-2-methyoxyphenyl octadecanoate.
Figure 28:
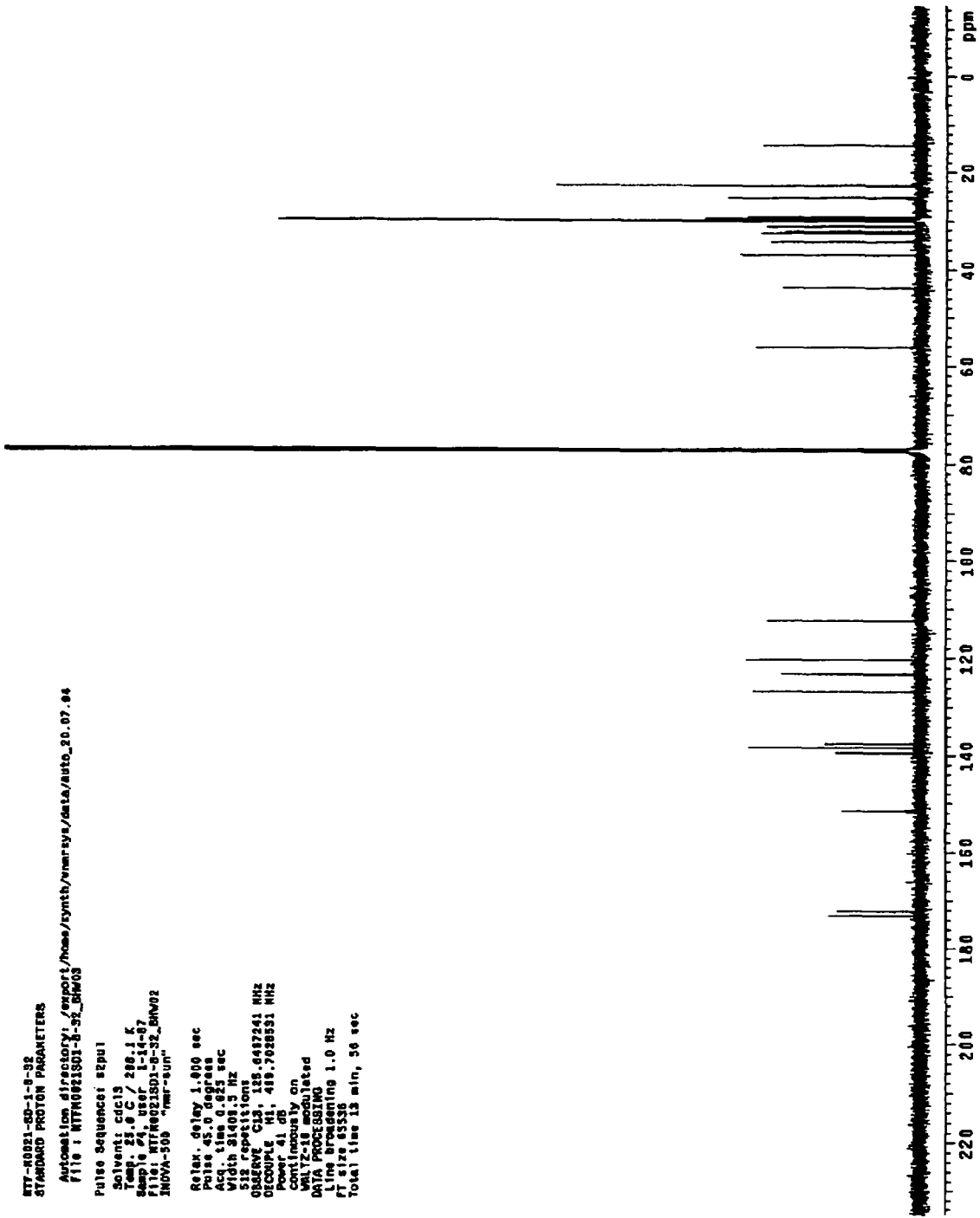
FIG. 28 provides a $^{13}$C-NMR of 4-[((6E)-8-methylnon-6-enoylamino)methyl]-2-methyoxyphenyl octadecanoate.
Figure 29:
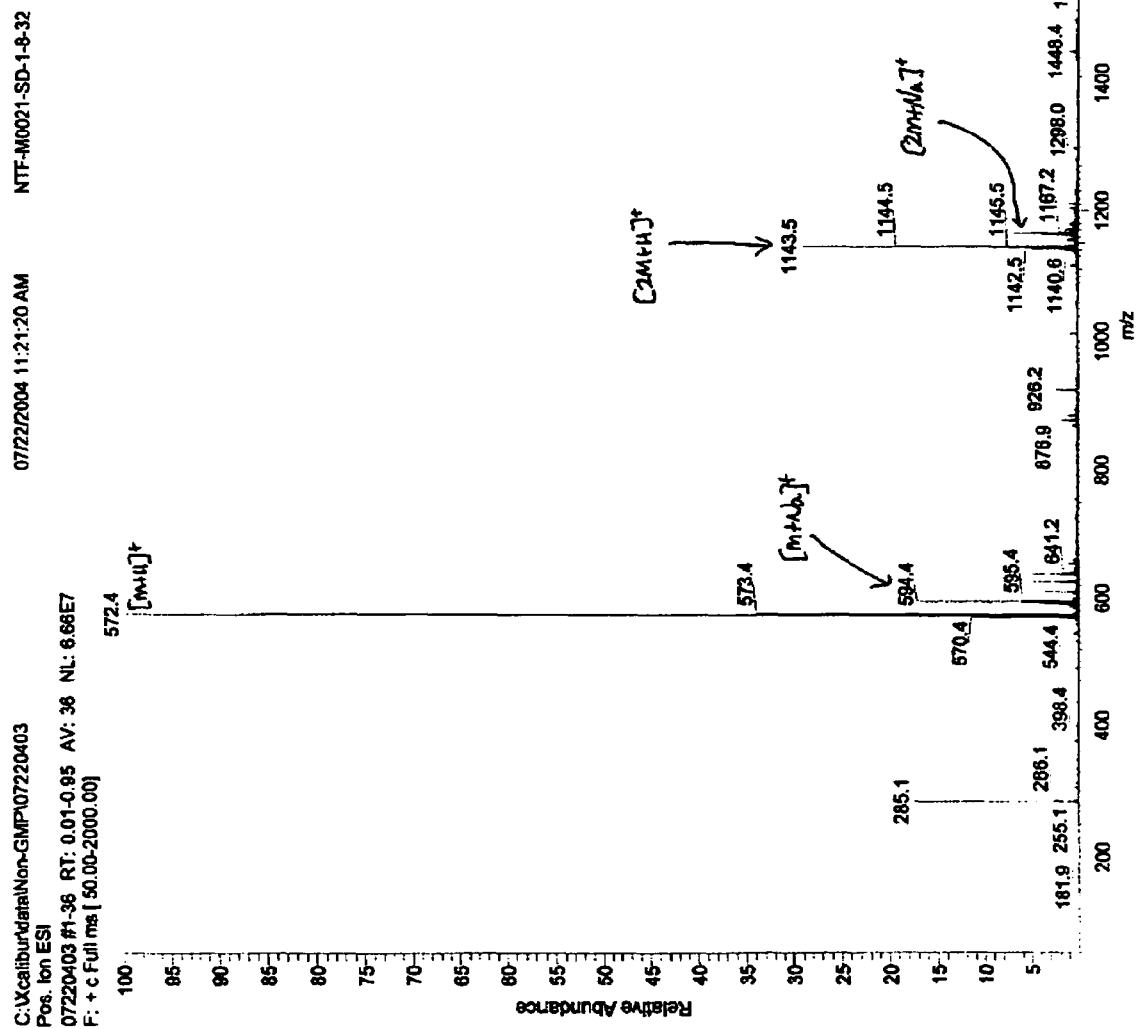
FIG. 29 is a mass spectrum of 4-[((6E)-8-methylnon-6-enoylamino)methyl]-2-methyoxyphenyl octadecanoate.
Figure 30:
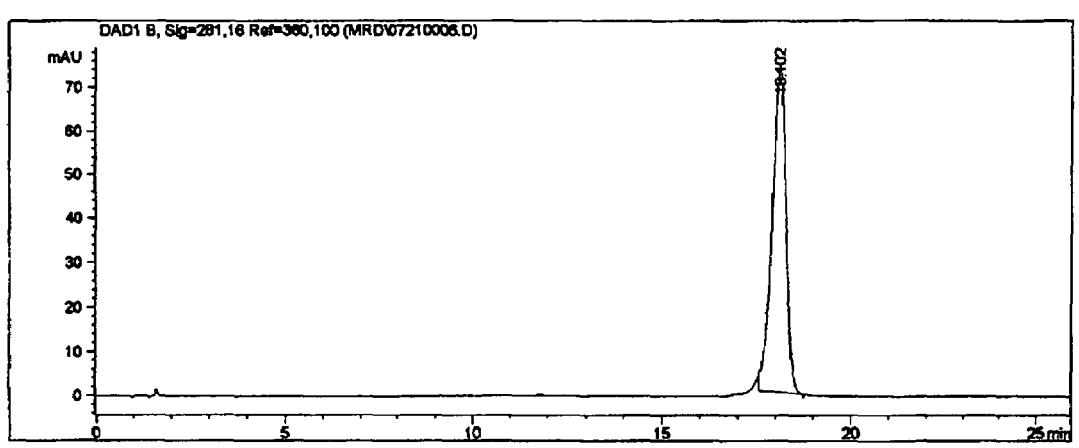
FIG. 30 provides an HPLC analysis of 4-[((6E)-8-methylnon-6-enoylamino)methyl]-2-methyoxyphenyl octadecanoate.

After the chromatography, 1.27 g of 4-[((6E)-8-methyl-non-6-enoylamino)methyl]-2-methyoxyphenyl octadecanoate was obtained in 97.0% yield as white solid. $^1$H-NMR and $^{13}$C-NMR were consistent with the desired structure (FIG. 27 and 28). Mass spectral analysis of the product was consistent with the desired structure (FIG. 29). HPLC analysis of the product showed 100.0% (AUC) purity (FIG. 30). Elemental analysis (FIG. 31) of the product was also consistent with the desired structure: Calculated for C$_{36}$H$_{61}$NO4: C, 75.61; H, 10.75; N, 2.45. Found: C, 75.60; H, 10.79; N, 2.44.

Example 7

Synthesis of a Macromolecular Conjugate Such as MonoPEGylated Capsaicin

A polyethylene glycol hydrolyzable ester conjugate of capsaicin or capsaicinoids may be prepared by a reaction of the aromatic hydroxyl group with the appropriate activated polyethylene glycol derivative. One such example is the esterification of mPEG succinamide with capsaicin as shown below.

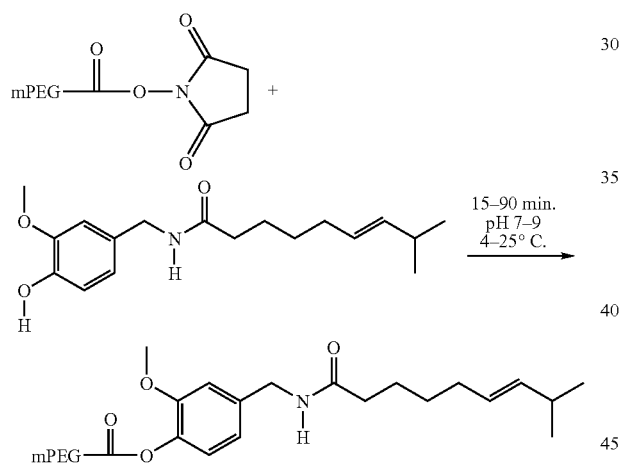

Figure 37:
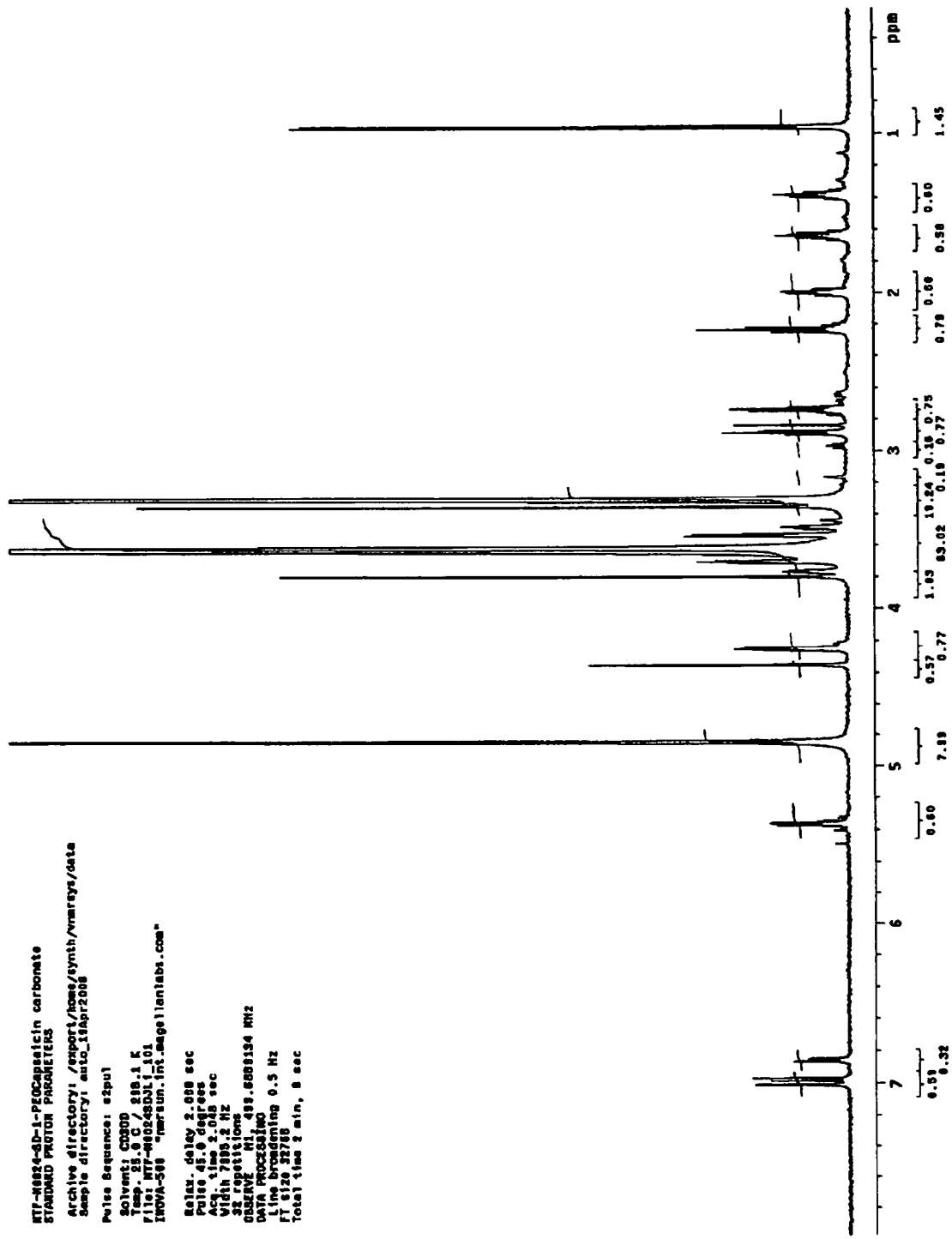
FIG. 37 provides a $^1$H-NMR of 4-[((6E)-8-methylnon-6-enoylamino)methyl]-2-methyoxyphenyl 2-[(2-methoxyethoxy)]$_n$ethyl butane-1,4-dioate

To a solution of capsaicin (160 mg, 0.5 mmol) and poly(ethylene glycol)(n)monomethyl ether mono(succinimidyl succinate)ester (Average MW=1900, 1.0 g, 0.5 mmol) in 10 mL of anhydrous dichloromethane was added triethyl amine (100 mg, 1 mmol) at ambient temperature. The reaction mixture was stirred at ambient temperature for 6 hours. TLC analysis of the reaction mixture indicated incompletion of the reaction (TLC condition: 10% methanol in DCM). 148 mg of diisopropyl ethyl amine (1.1 mmol) was added to the reaction mixture. The reaction mixture was stirred ambient temperature overnight. TLC analysis of the reaction mixture showed no progress of the reaction. The reaction mixture was diluted with DCM, washed with brine, dried over MgSO$_4$, concentrated to dryness. The obtained crude product was triturated with methyl tert-butyl ether to remove unreacted capsaicin. The collected white solid from filtration was dissolved in a small amount of DCM and loaded onto a silica gel column. The column was eluted with 5-10% of methanol in DCM. The fractions that contained pure product (as a single spot indicated by TLC) were combined and concentrated to dryness to give 395 mg of PEGylated capsaicin (40% yield) as a white solid. There were more fractions that contained the product as the major component along some impurities. $^1$H-NMR of the obtained PEGylated capsaicin was consistent with the desired structure (see FIG. 37)

Polyethylene glycol derivatives are available from Nektar Transforming Therapeutics, San Carlos, Calif. in various chain lengths and dispersions.

Example 8

Synthesis of a 4-[((6E)-8-methylnon-6-enoylamino)methyl]-2-methyoxyphenyl{4-[((6E)-8-methylnon-6-enoylamino)methyl]-2-methoxyphenoxy}formate (Gemini Dimer of Capsaicin)

Synthesis of carbonate linked capsaicin molecules may be done as follows.

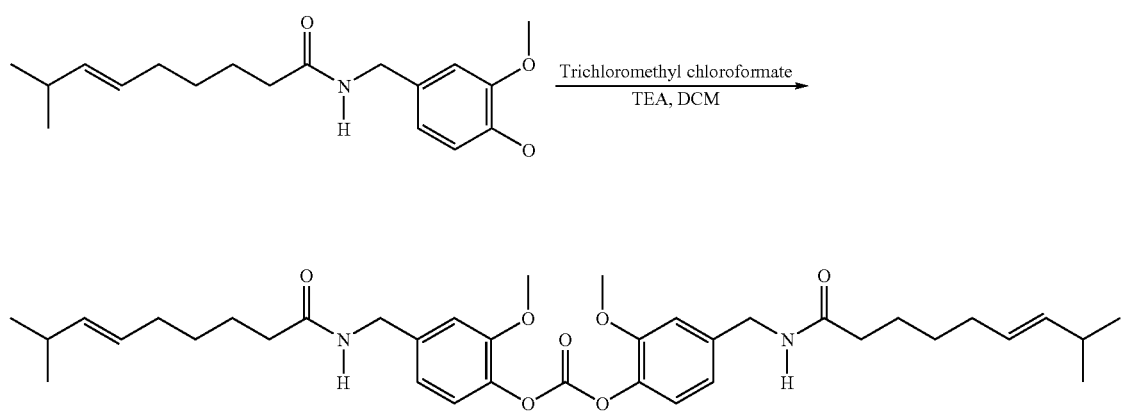

Figure 32:
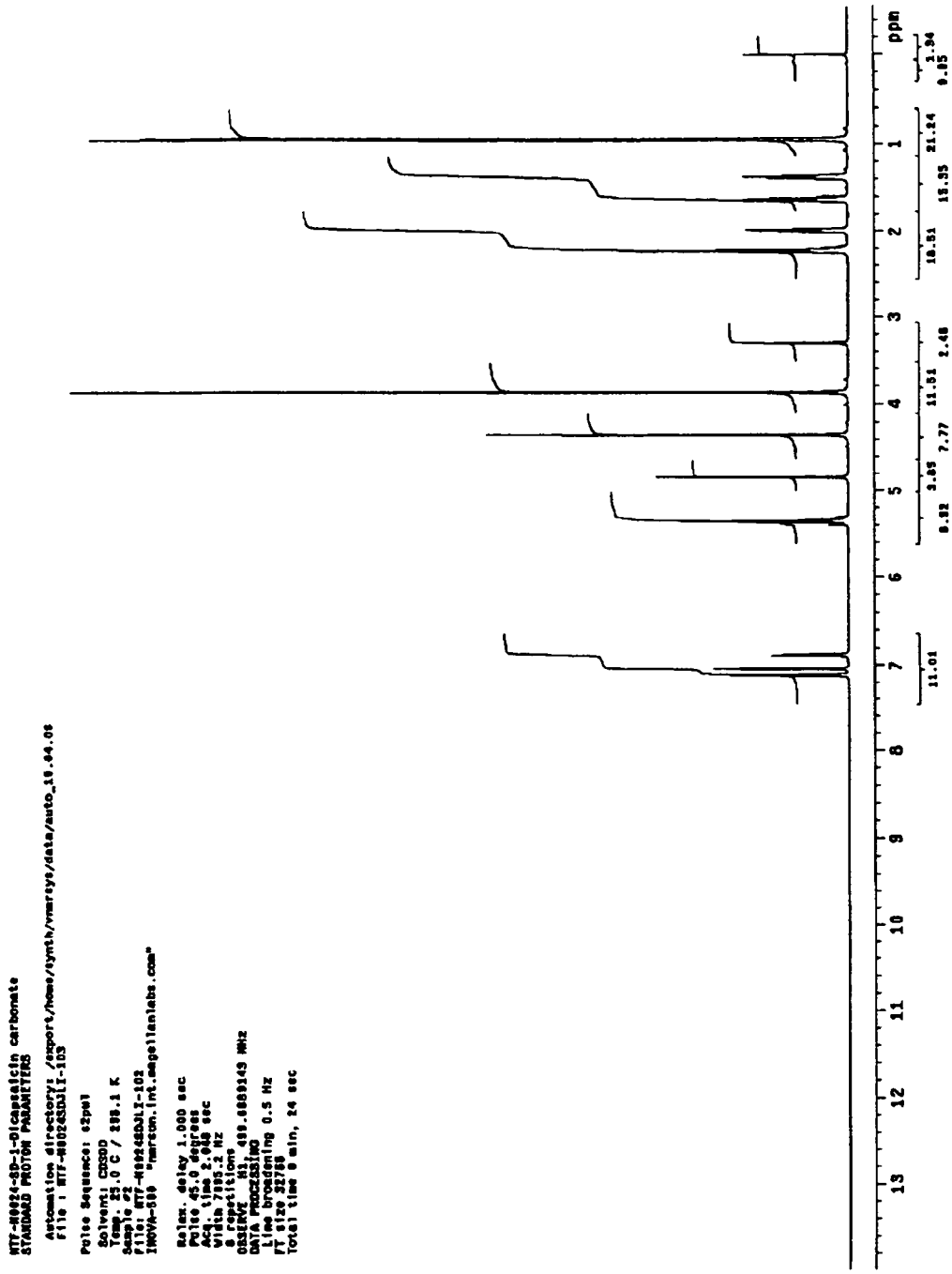
FIG. 32 provides a $^1$H-NMR of 4-[((6E)-8-methylnon-6-enoylamino)methyl]-2-methyoxyphenyl{4-[((6E)-8-methylnon-6-enoylamino)methyl]-2-methoxyphenoxy}formate FIG. 33 provides a $^{13}$C-NMR of 4-[((6E)-8-methylnon-6-enoylamino)methyl]-2-methyoxyphenyl{4-[((6E)-8-methylnon-6-enoylamino)methyl]-2-methoxyphenoxy}formate FIG. 34 provides a $^1$H-NMR of (1S,2S,5R)-5-methyl-2-(methylethyl)cyclohexyl{4-[((6E)-8-methylnon-6-enoylamino)methyl]-2-methyoxyphenyl formate FIG. 35 provides a $^{13}$C-NMR of (1S,2S,5R)-5-methyl-2-(methylethyl)cyclohexyl{4-[((6E)-8-methylnon-6-enoylamino)methyl]-2-methyoxyphenyl formate
Figure 33:
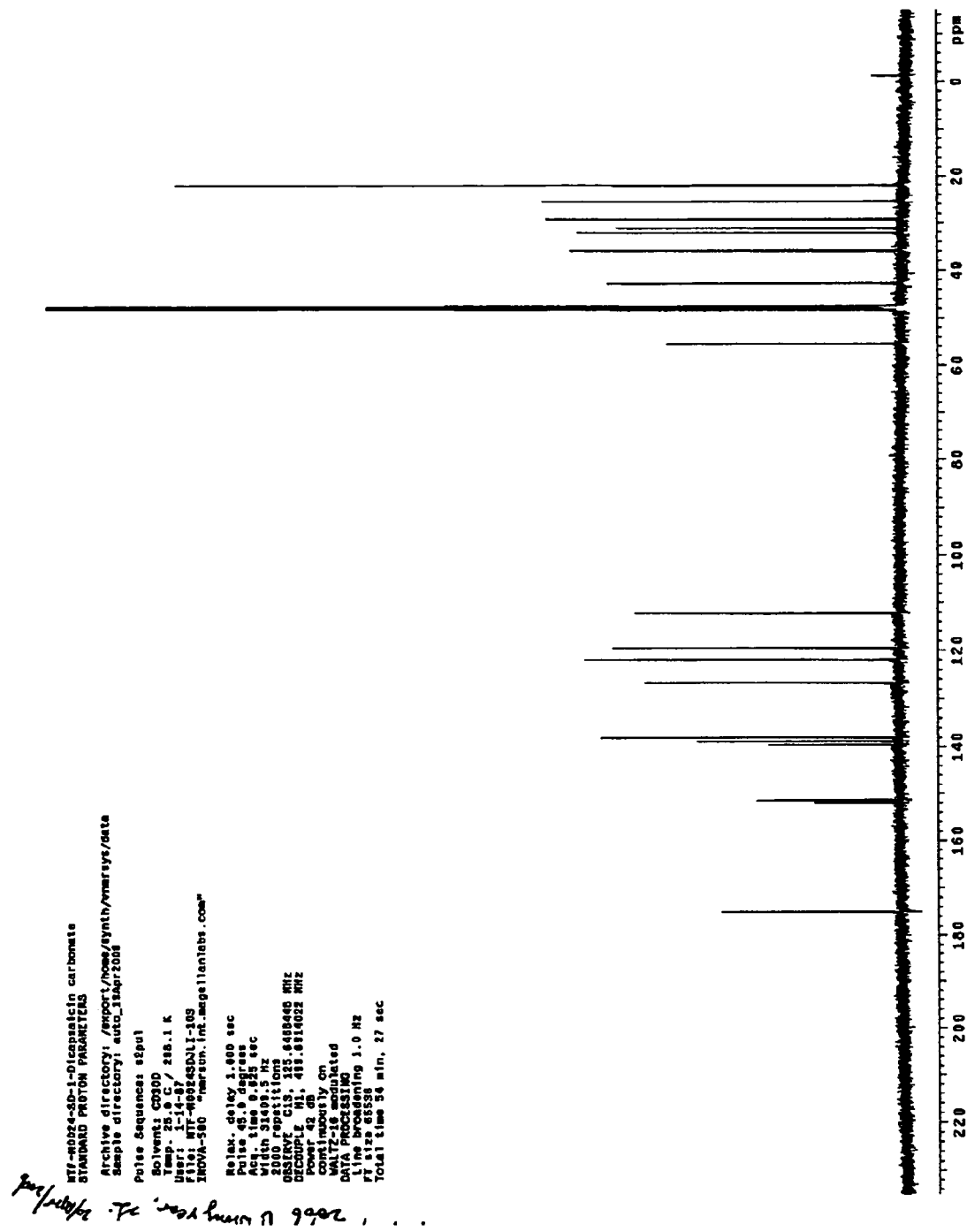

A solution of capsaicin (1.0 g, 3.3 mmol) in anhydrous dichloromethane (20 mL) was cooled to 0° C. by ice bath. To thistrichloromethyl chloroformate (162 mg, 0.82 mmol) at 0° C. was added, followed by the dropwise addition of triethylamine (1.98 g, 19.6 mmol). After the addition, the reaction mixture was stirred at 0° C. under nitrogen for 1 hour, then warmed up to ambient temperature for another 2 hours. The reaction mixture was diluted with dichloromethane (DCM), washed with 5% aqueous $K_2CO_3$ solution, brine, dried over $MgSO_4$, concentrated to dryness. The obtained crude product was purified via silica gel column chromatography (40%-80% ethyl acetate in hexane as the eluent) to give 0.9 g of gemini dimer of capsaicin (86.5% yield) as a white solid. $^1$H-NMR and $^{13}$C-NMR of the obtained gemini dimer of capsaicin were consistent with the desired structure (see FIGS. 32, 33).

Example 9

Synthesis of a (1S,2S5R)-5-methyl-2-(methylethyl) cyclohexyl{4-[((6E)-8-methylnon-6-enoylamino) methyl]-2-methyoxyphenyl formate (Capsaicin 1-Menthol Mutual Prodrug)

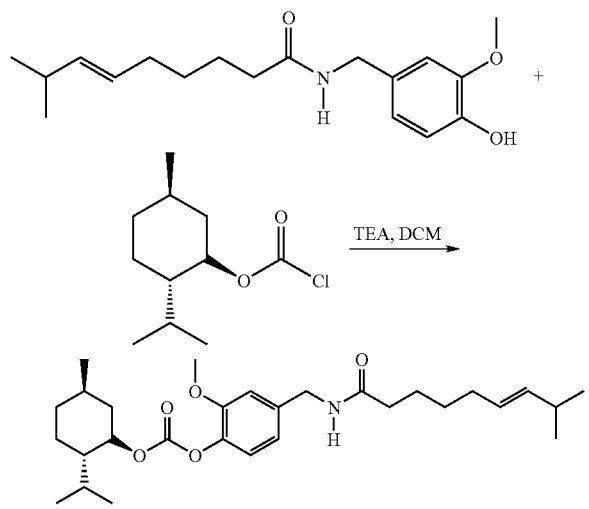

Figure 34:
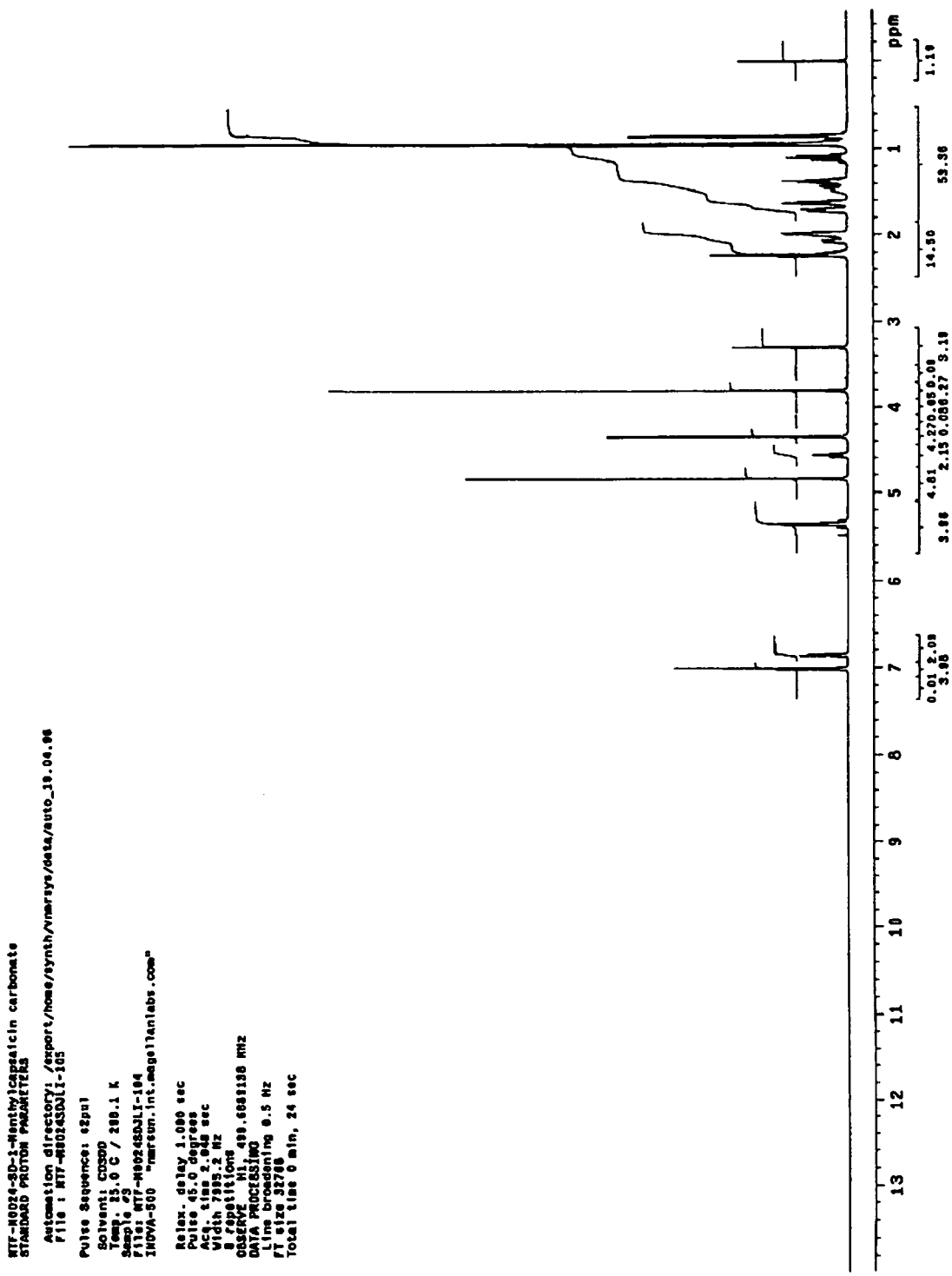
Figure 35:
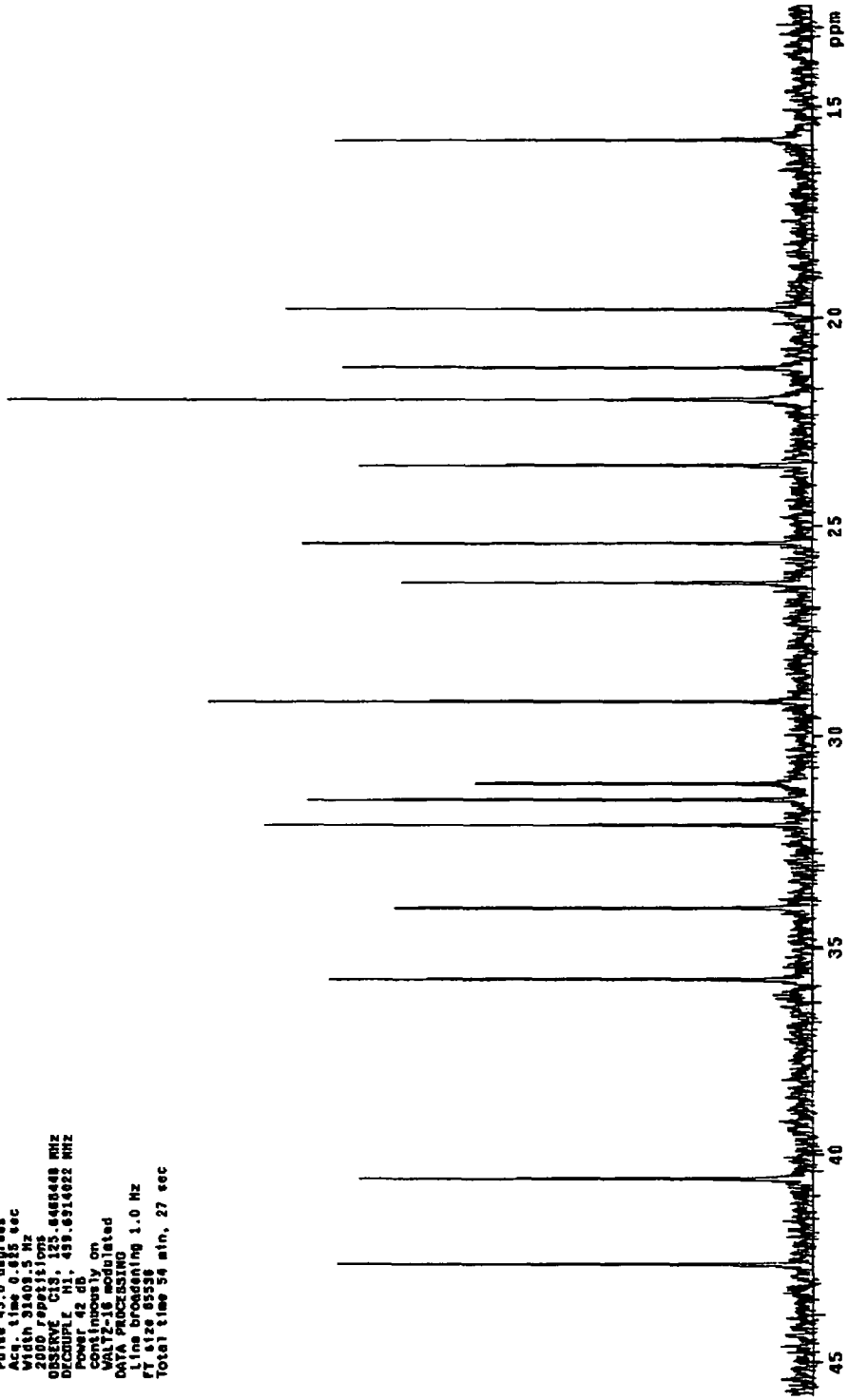
Figure 36:
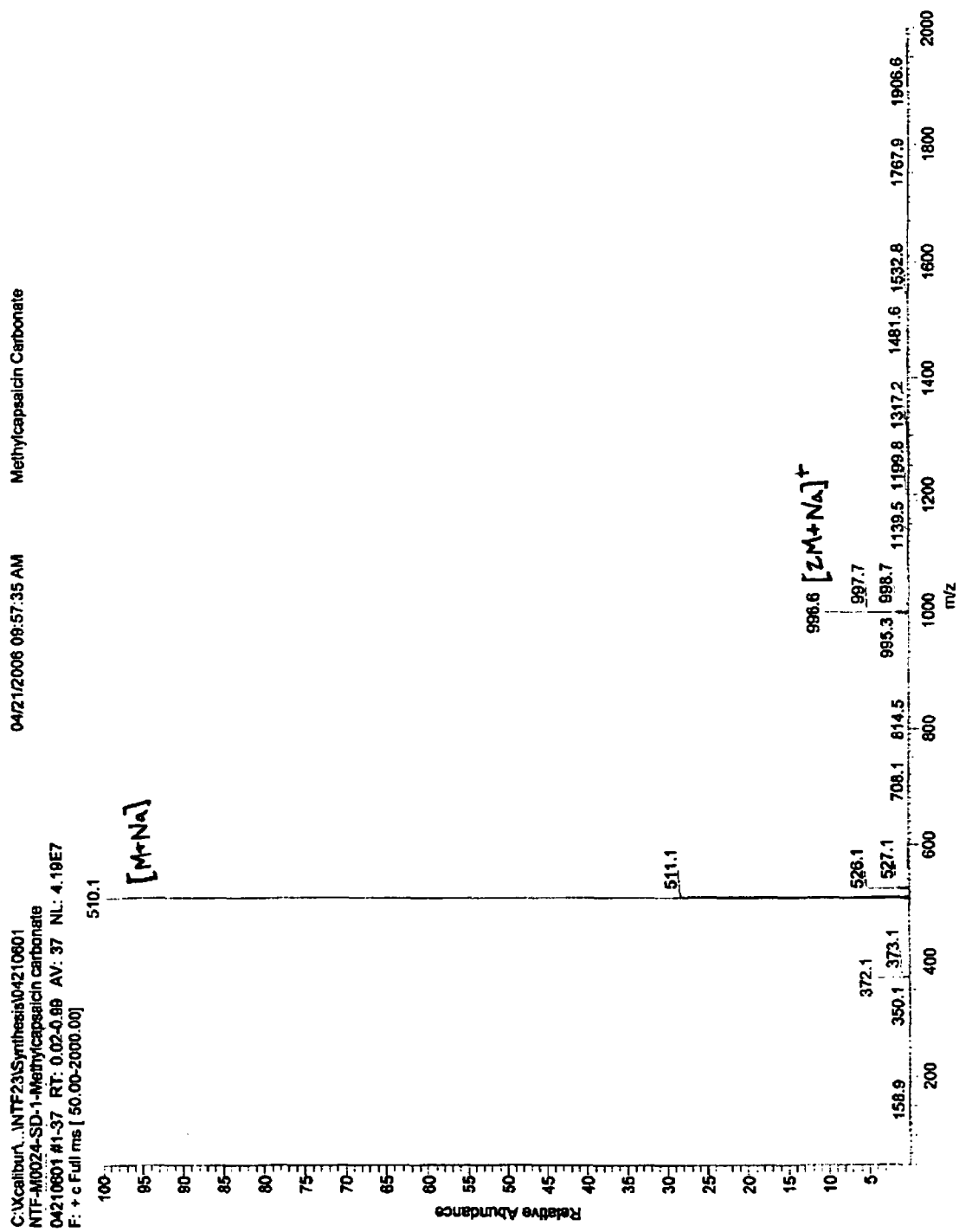
FIG. 36 is a mass spectrum of (1S,2S,5R)-5-methyl-2-(methylethyl)cyclohexyl{4-[((6E)-8-methylnon-6-enoylamino)methyl]-2-methyoxyphenyl formate.

To a solution of capsaicin (0.7 g, 2.3 mmol) and (−)-menthyl chloroformate (0.5 g, 2.3 mmol) in anhydrous dichloromethane (10 mL) was added triethylamine (0.45 g, 4.5 mmol) dropwise at ambient temperature. After the addition, the reaction mixture was stirred at ambient temperature for 2 hours. The reaction mixture was diluted with dichloromethane (DCM), washed with 5% aqueous $K_2CO_3$ solution, brine, dried over $MgSO_4$, concentrated to dryness. The obtained crude product was purified through silica gel column chromatography (30% -50% ethyl acetate in hexane as the eluent) to give 0.98 g of capsaicin 1-menthol mutual prodrug (87% yield) as clear viscous oil. $^1$H-NMR and $^{13}$C-NMR of the obtained capsaicin 1-menthol mutual prodrug were consistent with the desired structure (see FIGS. 34, 35). Mass spectral analysis of the product was consistent with the desired structure (FIG. 36).

V. ANALYSIS

The attached figures show various $^1$H- and $^{13}$C-NMR spectra, mass spectra, HPLC analysis, and elemental analysis of various compounds described herein.

HPLC Method: Altima $C_{18}$, 5 micron, 250×4.6 mm column. Mobile phase A: water containing 0.1% TFA. Mobile phase B: 0.1% TFA in acetonitrile. Injection volume: 20 μL. Sample concentration: 5 mg in 10 mL of acetonitrile. Flow rate: 1 ml/minute. HPLC column was used at ambient temperature.

$^1$H- and 13C-NMR Analysis: $^1$H- and $^{13}$C-NMR spectra were obtained using a 500 MHz FT-NMR spectrometer (Varian Instruments Anova).

What is claimed is:
1. A compound of the formula:

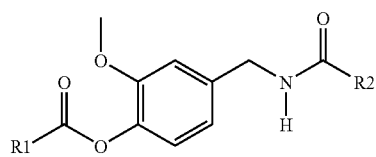

wherein R1 is selected from the group consisting of hydrogen, —(CH$_2$)$_n$CH$_3$ wherein n is an integer from 6-19, and a substituted, saturated or unsaturated, linear or branched, $C_1$-$C_{20}$ alkyl and R2 is selected from the group consisting of a substituted or unsubstituted, unsaturated, linear or branched $C_2$-$C_5$ alkyl, or (3E)-2-methyloct-3-ene, or (3Z)-2-methyloct-3-ene.

2. The compound of claim 1 wherein R1 is selected from the group consisting of hydrogen and a substituted, saturated or unsaturated, linear or branched, $C_1$-$C_{10}$ alkyl.

3. The compound of claim 1 wherein R1 is —(CH$_2$)$_n$CH$_3$ and n is an integer from 6-19.

4. The compound of claim 3 wherein n is an integer from 6-10.

5. The compound of claim 3 wherein n is an integer from 11-19.

6. The compound of claim 1 wherein R2 is (3E)-2-methyloct-3-ene.

7. The compound of claim 1 wherein R2 is (3Z)-2-methyloct-3-ene.

8. A formulation comprising the compound of claim 1, wherein the formulation is a liquid, tablet, capsule, gel, cream, emulsion or patch.

9. A compound of the formula:

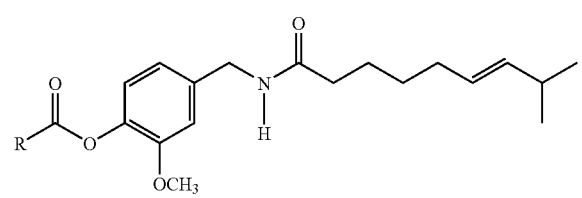

where R is selected from the group consisting of hydrogen, —(CH$_2$)$_n$CH$_3$ wherein n is an integer from 6-19, and a substituted, saturated or unsaturated, linear or branched, $C_2$-$C_{20}$ alkyl.

10. A formulation comprising the compound of claim 9, wherein the formulation is a liquid, tablet, capsule, gel, cream, emulsion or patch.

11. A compound of the formula:

[chemical structure]

where R is selected from the group consisting of hydrogen, —(CH$_2$)$_n$CH$_3$ wherein n is an integer from 6-19, and a substituted, saturated or unsaturated, linear or branched C$_2$-C$_{20}$ alkyl.

12. A formulation comprising the compound of claim 11, wherein the formulation is a liquid, tablet, capsule, gel, cream, emulsion or patch.

13. A compound of the formula:

[chemical structure]

where R is selected from the group consisting of hydrogen, —(CH$_2$)$_n$CH$_3$ wherein n is an integer from 6-19, and a substituted, unsaturated, linear or branched, C$_2$-C$_{20}$ alkyl.

14. A formulation comprising the compound of claim 13, wherein the formulation is a liquid, tablet, capsule, gel, cream, emulsion or patch.

15. A TRPV1 agonist prodrug comprising:
a TRPV1 agonist modified by covalent attachment of a prodrug moiety, wherein the prodrug moiety restricts binding to or activation of the TRPV1 receptor wherein the TRPV1 agonist is selected from the group consisting of civamide, olvanil, and resiniferatoxin.

16. The TRPV1 agonist prodrug of claim 15 wherein the TRPV1 agonist is a civamide.

17. The TRPV1 agonist prodrug of claim 15 wherein the TRPV1 agonist is olvanil.

18. The TRPV1 agonist prodrug of claim 15 wherein the prodrug moiety is attached to the TRPV1 agonist by substitution of the phenolic hydrogen of the TRPV1 agonist with the prodrug moiety.

19. The TRPV1 agonist prodrug of claim 18 wherein the prodrug moiety is an acyl or an alkoxy.

20. The TRPV1 agonist prodrug of claim 19 wherein the prodrug moiety is an acyl.

21. A formulation comprising the TRPV1 agonist prodrug of claim 15, wherein the formulation is a liquid, tablet, capsule, gel, cream, emulsion or patch.

22. A microreservoir, monolithic, or liquid reservoir patch comprising a compound of the-formula:

[chemical structure]

wherein R1 is selected from the group consisting of hydrogen and a substituted or unsubstituted, saturated or unsaturated, linear or branched, C$_1$-C$_{20}$ alkyl and R2 is selected from the group consisting of a substituted or unsubstituted, saturated or unsaturated, linear or branched C$_1$-C$_{20}$ alkyl.

23. A patch comprising the compound of claim 9.

24. A patch comprising the compound of claim 11.

25. A microreservoir, monolithic, or liquid reservoir patch comprising a compound of the formula:

[chemical structure]

where R is selected from the group consisting of hydrogen and a substituted or unsubstituted, saturated or unsaturated, linear or branched, C$_2$-C$_{20}$ alkyl.

26. A patch comprising the TRPV1 agonist prodrug of claim 15.

27. A pharmaceutical formulation comprising a capsaicin or capsaicinoid prodrug wherein the capsaicin or capsaicinoid prodrug comprises:
capsaicin or a capsaicinoid modified by covalent attachment of a prodrug moiety, wherein the prodrug moiety facilitates sustained release of capsaicin or the capsaicinoid.

28. The prodrug of claim 27 wherein the prodrug moiety is attached to the capsaicin or capsaicinoid by substitution of the phenolic hydrogen of cap saicin or capsaicinoid with the prodrug moiety.

29. A prodrug of claim 27 wherein the prodrug moiety is m-PEG.

30. A mutual prodrug comprising capsaicin covalently linked to at least one other compound wherein the at least one other compound is capable of treating pain.

31. The mutual prodrug of claim 30 wherein the at least one other compound is l-menthol.

32. The mutual prodrug of claim 30 wherein the at least one other compound is a COX inhibitor.

33. The mutual prodrug of claim 30 wherein the at least one other compound is an opioid analgesic.

34. A formulation comprising the mutual prodrug of claim 30, wherein the formulation is a liquid, tablet, capsule, gel, cream, emulsion or patch.

35. A composition comprising a gemini dimer of a TRPV1 agonist.

36. The composition of claim 35 wherein the TRPV1 agonist is a capsaicinoid.

37. The composition of claim 35 wherein the TRPV1 agonist is capsaicin.

38. The composition of claim 35 wherein the gemini dimer is composed of two different TRPV1 agonists.

39. A formulation comprising the composition of claim 35, wherein the formulation is a liquid, tablet, capsule, gel, cream, emulsion or patch.

40. A method for treating pain comprising the step of locally, dermally, transdermally or systemically delivering the compound of claim 1, the compound of claim 9, the compound of claim 11, the compound of claim 13, the prodrug of claim 15, the prodrug of claim 27, the mutual prodrug of claim 30, or the composition of claim 35.

41. The method of claim 40 wherein the pain is associated with postherpetic neuralgia, diabetic neuropathy, HIV-associated neuropathy, complex regional pain syndrome, cancer, nerve injury, cancer chemotherapy, vulvodynia, trauma, surgery, chronic musculoskeletal pain, lower back pain, osteoarthritis or rheumatoid arthritis.

42. The method of claim 40 wherein the medical condition to be treated is selected from the group consisting of psoriasis, pruritis, itch, cancer, colon polyps, prostatic hypertrophy, wrinkles, sinusitis, rhinitis, alopecia and hirsutism.

43. A compound of claim 1 wherein the compound is a TRPV1 agonist prodrug.

44. A compound of claim 9 wherein the compound is a TRPV1 agonist prodrug.

45. A compound of claim 11 wherein the compound is a TRPV1 agonist prodrug.

46. A compound of claim 13 wherein the compound is a TRPV1 agonist prodrug.

* * * * *